(12) United States Patent
Ducharme et al.

(10) Patent No.: US 6,486,194 B2
(45) Date of Patent: Nov. 26, 2002

(54) USE OF INHIBITORS OF CYCLOOXYGENASE IN THE TREATMENT OF NEURODEGENERATIVE DISEASES

(75) Inventors: Yves Ducharme, Montreal (CA); Jacques Yves Gauthier, Laval (CA); Petpiboon Prasit, Kirkland (CA); Yves Leblanc, Kirkland (CA); Zhaoyin Wang, Pierrefonds (CA); Serge Leger, Dollard des Ormeaux (CA); Michel Therien, Dollard des Ormeaux (CA)

(73) Assignee: Merck Frosst Canada, Inc., Kirkland (CA)

( * ) Notice: Subject to any disclaimer, the term of this patent is extended or adjusted under 35 U.S.C. 154(b) by 0 days.

(21) Appl. No.: 09/796,211

(22) Filed: Feb. 28, 2001

(65) Prior Publication Data

US 2001/0016595 A1 Aug. 23, 2001

Related U.S. Application Data

(63) Continuation of application No. 09/552,974, filed on Apr. 20, 2000, now abandoned, which is a continuation of application No. 09/161,516, filed on Sep. 28, 1998, now abandoned, which is a continuation-in-part of application No. 08/539,930, filed on Oct. 6, 1995, now abandoned, which is a continuation-in-part of application No. 08/461,783, filed on Jun. 5, 1995, now abandoned, which is a continuation-in-part of application No. 08/179,467, filed on Jan. 10, 1994, now Pat. No. 5,474,995, which is a continuation-in-part of application No. 08/082,196, filed on Jun. 24, 1993, now abandoned.

(30) Foreign Application Priority Data

Oct. 12, 1994 (GB) .............................. 9420616

(51) Int. Cl.$^7$ ................................ A61K 31/38
(52) U.S. Cl. ................ 514/438; 514/365; 514/372; 514/461; 514/473; 514/484
(58) Field of Search ................ 574/438; 514/438, 514/365, 372, 473, 461, 484

(56) References Cited

PUBLICATIONS

The Merck Manual, "Disorders, Cerebral Hemispheres and Higher Brain Functions", (1987), p. 1337, Fifteenth Edition.

*Primary Examiner*—Amelia Owens
(74) *Attorney, Agent, or Firm*—Curtis C. Panzer; David L. Rose

(57) ABSTRACT

The present invention provides a method of treating a neurodegenerative disease and in particular Alzheimers disease which comprises administering to a human in need thereof a therapeutically effective amount of a non-steroid COX-II inhibitor. Although a wide range of COX-II inhibitors may be employed but it is preferred to employ compounds of the Formula I:

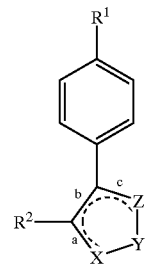

6 Claims, No Drawings

USE OF INHIBITORS OF CYCLOOXYGENASE IN THE TREATMENT OF NEURODEGENERATIVE DISEASES

RELATED US APPLICATION DATA

This is a continuation of application Ser. No. 09/552,974, filed Apr. 20, 2000, now abandoned, which is a continuation of application Ser. No. 09/161,516, filed Sep. 28, 1998, now abandoned, which is a continuation in part of U.S. Ser. No. 08/539,930 filed Oct. 6, 1995 now abandoned which is a continuation in part of U.S. Ser. No. 08/461,783 filed Jun. 5, 1995 now abandoned which is a continuation-in-part of 08/179,467 filed Jan. 10, 1994 now U.S. Pat. No. 5,474,995 which is a continuation-in-part of U.S. Ser. No. 08/082,196 filed Jun. 24, 1993 now abandoned.

BACKGROUND TO THE INVENTION

U.S. Pat. No. 5,192,753 states inter alia that dementia in human beings may be treated with compounds selected from the non-steroidal anti-inflammatory group of cyclooxygenase inhibitors. The non-steroid anti-inflammatory drugs (NSAIDs) referred to in U.S. Pat. No. 5,192,753 are all agents which possess significant ability to inhibit cyclooxygenase type 1 (COX-1). A number of publications have also occurred in the scientific literature which disclose that agents such as acetylacetic acid and indomethecin, which are generally viewed as potent inhibitors of COX-1, can be used in the treatment of Alzheimers disease; see for example:

McGeer et al, *Lancet,* 1990:335, 1037;

Rogers et al, *Neurology,* 1993:43; 1609–1611;

McGeer et al, *Neurology,* 1992:42, 447–449; and

Breitner et al, *Neurology,* 1994, 227–232.

Cyclooxygenase (COX) exists in the human as cyclooxygenase type I (COX-I) and cyclooxygenase type II (COX-II also referred to herein as COX-2). Hitherto there has been no suggestion that COX-II plays any role in Alzheimers disease. Indeed there has been no evidence which demonstrates that COX-II plays a part in any human central nervous system disorder. COX-II is inducilible by a number of agents such as mitogen, endotoxin, cytokines and the like but none of these agents which have been demonstrated as inducing COX-II have been shown to be causitive in Alzheimers disease.

Non-steroidal, antiinflammatory drugs exert most of their antiinflammatory, analgesic and antipyretic activity and inhibit hormone-induced uterine contractions and certain types of cancer growth through inhibition of prostaglandin G/H synthase, also known as cyclooxygenase. Up until recently, only one form of cyclooxygenase had been characterized, this corresponding to cyclooxygenase-1 or the constitutive enzyme, as originally identified in bovine seminal vesicles. Recently the gene for a second inducible form of cyclooxygenase (cyclooxygenase-2) has been cloned, sequenced and characterized from chicken, murine and human sources. This enzyme is distinct from the cyclooxygenase-1 which has now also been cloned, sequenced and characterized from sheep, murine and human sources. The second form of cyclooxygenase, cyclooxygenase-2, is rapidly and readily inducible by a number of agents including mitogens, endotoxin, hormones, cytokines and growth factors. As prostaglandins have both physiological and pathological roles, we have concluded that the constitutive enzyme, cyclooxygenase-1, is responsible, in large part, for endogenous basal release of prostaglandins and hence is important in their physiological functions such as the maintenance of gastrointestinal integrity and renal blood flow. In contrast, we have concluded that the inducible form, cyclooxygenase-2, is mainly responsible for the pathological effects of prostaglandins where rapid induction of the enzyme would occur in response to such agents as inflammatory agents, hormones, growth factors, and cytokines. Thus, a selective inhibitor of cyclooxygenase-2 will have similar antiinflammatory, antipyretic and analgesic properties to a conventional non-steroidal antiinflammatory drug, and in addition would inhibit hormone-induced uterine contractions and have potential anti-cancer effects, but will have a diminished ability to induce some of the mechanism-based side effects. In particular, such a compound should have a reduced potential for gastrointestinal toxicity, a reduced potential for renal side effects, a reduced effect on bleeding times and possibly a lessened ability to induce asthma attacks in aspirin-sensitive asthmatic subjects.

The present invention provides a method of treating a neurodegenerative disease and in particular Alzheimers disease which comprises administering to a human in need thereof a therapeutically effective amount of a non-steroid COX-II inhibitor.

SUMMARY OF INVENTION

The present invention provides a method of treating a neurodegenerative disease and in particular Alzheimers disease which comprises administering to a human in need thereof a therapeutically effective amount of a non-steroid COX-II inhibitor. Although a wide range of COX-II inhibitors may be employed but it is preferred to employ compounds of the Formula I as set out hereinafter.

DETAILED DESCRIPTION OF THE INVENTION

In one aspect the invention encompasses a method of treating a neurodegenerative disease in a human which comprises administering to said human an effective amount of a non-steroidal COX-2 inhibitor.

Within this apsect the invention encompasses a method of treating the neurodegenerative disease, Alzheimers Disease.

Within the above aspect the invention also encompasses a method of treating stroke, cerebral ischernia and de-myelinating disorders.

Oral administration (such as by tablet or capsule) is a preferred mode of administration Within the above aspect, there is a preferred classs of method wherein the non-steroidal COX-2 inhibitor will bind at least 100 times as well to COX-2 as to COX-1.

Within the above aspect there is a preferred class of COX-2 inhibitors, which is:

(a) 3-(4-(Aminosulfonyl) phenyl)-2-(4-fluorophenyl)-5-(2-hydroxy-2-propyl)thiophene, (b) 3-(4-(Aminosulfonyl) phenyl)-2-(4-fluorophenyl) thiophene, (c) 3-(4-(Aminosulfonyl)phenyl)-2-(4-fluorophenyl)-5-(2-propyl)thiophene, (d) 3-(4-(Aminosulfonyl)phenyl)-2-cyclohexylthiophene, (e) 5-(4-Carboxyphenyl)-4-(4-(methylsulfonyl)phenyl) thiophene-2-carboxylic acid, (f) 4-(4-Fluorophenyl)-2-methyl-5-(4-(methylsulfonyl) phenyl)thiazole, (g) 2-(4-Fluorophenyl)-3-(4-(methylsulfonyl)phenyl)-2-cyclopenten-1-one (h) 4-(4-(Methylsulfonyl)phenyl)-5-(4-fluorophenyl)-isothiazole, (i) 3-(4-Fluorophenyl)-4-(4-(methylsulfonyl)phenyl)-2-(5H)-furanone,
(j) 3-(4-Fluorophenyl)-4-(4-(aminosulfonyl)phenyl)-2-(5H)-furanone,
(k) 3-(4-Fluorophenyl)-4-(4-(methylsulfonyl)phenyl) furan,
(l) 5,5-Dimethyl-3-(4-fluorophenyl)-4-(4-methylsulfonyl)phenyl)-2-(5H)-furanone,
(m) 2-(4-(Aminosulfonyl)phenyl)-3-(4-fluorophenyl) thiophene,
(n) 3-(4-(Trifluoroacetylaminosulfonyl)phenyl)-2-(4-fluorophenyl)thiophene,
(o) 3-(3-Fluorophenyl)-4-(4-(methylsulfonyl)phenyl)-2-(5H)-furanone,
(p) 5,5-Dimethyl-3-(3fluorophenyl)-4-(4-methylsulfonyl)phenyl)-2-(5H)-furanone,
(q) 5,5-Dimethyl-3-(3-chlorophenyl)-4-(4-methylsulfonyl) phenyl)-2-(5H)-furanone,
(r) 3-(3,4-Difluorophenyl)-4-(4-(methylsulfonyl)phenyl)-2-(5H)-furanone,
(s) 3-(3,4-Dichlorophenyl)-4-(4-(methylsulfonyl) phenyl)-2-(5H)-furanone,
(t) 5,5-Dimethyl-3-(3,4-difluorophenyl)-4-(4-methylsulfonyl)phenyl)-2-(5H)-furanone,
(u) 5,5-Dimethyl-3-(3,4-dichlorophenyl)-4-(4-methylsulfonyl)phenyl)-2-(5H)-furanone,
(v) 5,5-Dimethyl-3-(4-chlorophenyl)-4-(4-methylsulfonyl)phenyl)-2-(5H)-furanone,
(w) 3-(2-Naphyhyl)-4-(4-(methylsulfonyl)phenyl)-2-(5H)-furanone,
(x) 5,5-Dimethyl-3-(2-naphyhyl)-4-(4-(methylsulfonyl)phenyl)-2-(5H)-furanone, and
(y) 3-phenyl-4-(4-(methylsulfonyl)phenyl)-2-(5H)-furanone.

The invention also encompasses the novel compound of Formula I useful in the treatment of cyclooxygenase-2 mediated diseases

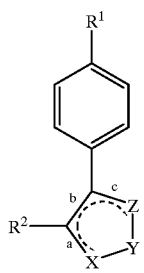

I or pharmaceutically acceptable salts thereof wherein:
X-Y-Z-is selected from the group consisting of:
(a) —$CH_2CH_2CH_2$—,
(b) —C(O)$CH_2CH_2$—,
(c) —$CH_2CH_2$C(O)—,
(d) —$CR^5(R^{5'})$—O—C(O)—,
(e) —C(O)—O—$CR^5(R^{5'})$—,
(f) —$CH_2$—$NR^3$—$CH_2$—,
(g) —$CR^5(R^{5'})$—$NR^3$—C(O)—,
(h) —$CR^4$=$CR^{4'}$—S—,
(i) —S—$CR^4$=$CR^{4'}$—,
(j) —S—N=CH—,
(k) —CH⊙N—S—,
(l) —N=$CR^4$—O—,
(m) —O—$CR^4$=N—
(n) —N=$CR^4$—NH—;
(o) —N=$CR^4$—S—, and
(p) —S—$CR^4$=N—;
(q) —C(O)—$NR^3$—$CR^5(R^{5'})$—;
(r) —$R^3$N—CH=CH— provided $R^1$ is not —$S(O)_2$Me
(s) —CH=CH—$NR^3$— provided $R^1$ is not —$S(O)_2$Me
when side b is a double bond, and sides a an c are single bonds; and
X-Y-Z-is selected from the group consisting of:
(a) =CH—O—CH=, and
(b) =CH—$NR^3$—CH=,
(c) =N—S—CH=,
(d) =CH—S—N=,
(e) =N—O—CH=,
(f) =CH—O—N=,
(g) =N—S—N=,
(h) =N—O—N=,
when sides a and c are double bonds and side b is a single bond;
$R^1$ is selected from the group consisting of
(a) $S(O)_2CH_3$,
(b) $S(O)_2NH_2$,
(c) $S(O)_2NHC(O)CF_3$,
(d) S(O)H)$CH_3$,
(e) S(O)(NH)$NH_2$,
(f) S(O)(NH)NHC(O)$CF_3$,
(g) P(O)($CH_3$)OH, and
(h) P(O)($CH_3$)$NH_2$,
$R^2$ is selected from the group consisting of
(a) $C_{1-6}$alkyl,
(b) $C_3$, $C_4$, $C_5$, $C_6$, and $C_7$, cyloalkyl,
(c) mono-, di- or tri-substituted phenyl or naphthyl wherein the substituent is selected from the group consisting of
(1) hydrogen,
(2) halo,
(3) $C_{1-6}$alkoxy,
(4) $C_{1-6}$alkylthio,
(5) CN,
(6) $CF_3$,
(7) $C_{1-6}$alkyl,
(8) $N_3$,
(9) —$CO_2$H,
(10) —$CO_2$—$C_{1-4}$alkyl,
(11) —C($R^5$)($R^6$)—OH,
(12) —C($R^5$)($R^6$)—O—$C_{1-4}$alkyl, and
(13) —$C_{1-6}$alkyl—$CO_2$—$R^5$;
(d) mono-, di- or tri-substituted heteroaryl wherein the heteroaryl is a monocyclic aromatic ring of 5 atoms, said ring having one hetero atom which is S, O, or N, and optionally 1, 2, or 3 additionally N atoms; or the heteroaryl is a monocyclic ring of 6 atoms, said ring having one hetero atom which is N, and optionally 1, 2, 3, or 4 additional N atoms; said substituents are selected from the group consisting of
(1) hydrogen,
(2) halo, including fluoro, chloro, bromo and iodo,
(3) $C_{1-6}$alkyl,
(4) $C_{1-6}$alkoxy, (5) $C_{1-6}$alkylthio,
(6) CN,
(7) $CF_3$,
(8) $N_3$,
(9) —$C(R^5)(R^6)$—OH, and
(10) —$C(R^5)(R^6)$—O—$C_{1-4}$alkyl;
(e) benzoheteroaryl which includes the benzo fused analogs of (d);

$R^3$ is selected from the group consisting of
(a) hydrogen,
(b) $CF_3$,
(c) CN,
(d) $C_{1-6}$alkyl,
(e) hydroxy$C_{1-6}$alkyl,
(f) —C(O)—$C_{1-6}$alkyl,
(g) optionally substituted
   (1) —$C_{1-5}$ alkyl-Q,
   (2) —$C_{1-3}$alkyl—O—$C_{1-3}$ alkyl—Q,
   (3) —$C_{1-3}$ alkyl—S—$C_{1-3}$ alkyl—Q,
   (4) —$C_{1-5}$ alkyl—O—Q, or
   (5) —$C_{1-5}$ alkyl—S—Q,
   wherein the substituent resides on the alkyl and the substituent is $C_{1-3}$alkyl;
(h) —Q $R^4$ and $R^{4'}$ are each independently selected from the group consisting of
(a) hydrogen,
(b) $CF_3$,
(c) CN,
(d) $C_{1-6}$alkyl,
(e) —Q,
(f) —O—Q;
(g) —S—Q, and
(h) optionally substituted
   (1) —$C_{1-5}$ alkyl—Q,
   (2) —O—$C_{1-5}$ alkyl—Q,
   (3) —S—$C_{1-5}$ alkyl—Q,
   (4) —$C_{1-3}$alkyl—O—$C_{1-3}$alkyl—Q,
   (5) —$C_{1-3}$alkyl—S—$C_{1-3}$alkyl—Q,
   (6) —$C_{1-5}$ alkyl—O—Q,
   (7) —$C_{1-5}$ alkyl—S'Q,
   wherein the substituent resides on the alkyl and the substituent is $C_{1-3}$alkyl, and $R^5$, $R^{5'}$, $R^6$, $R^7$ and $R^8$ are each independently selected from the group consisting of
(a) hydrogen,
(b) $C_{1-6}$alkyl,
or $R^5$ and $R^6$ or $R^7$ and $R^8$ together with the carbon to which they are attached form a saturated monocyclic carbon ring of 3, 4, 5, 6 or 7 atoms;

Q is $CO_2H$, $CO_2$—$C_{1-4}$alkyl, tetrazolyl-5-yl, $C(R^7)(R^8)$(OH), or $C(R^7)(R^8)(O$—$C_{1-4}$alkyl);

provided that when X—Y—Z is —S—$CR^4$=$CR^{4'}$, then $R^4$ and $R^{4'}$ are other than $CF_3$.

One Class within this embodiment are the compounds of formula I

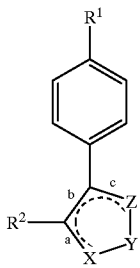

or pharmaceutically acceptable salts thereof wherein:
X—Y—Z— is selected from the group consisting of —C(O)—O—$CR^5(R^{5'})$— when side b is a double bond, and sides a and c are single bonds; and $R^1$ is selected from the group consisting of
(a) $S(O)_2CH_3$,
(b) $S(O)_2NH_2$, $R^2$ is selected from the group consisting of
(a) $C_{1-6}$alkyl,
(b) $C_3$, $C_4$, $C_5$, $C_6$, and $C_7$, cycloalkyl,
(c) heteroaryl
(d) benzoheteroaryl
(e) mono- or di-substituted phenyl wherein the substituent is selected from the group consisting of
   (1) hydrogen,
   (2) halo,
   (3) $C_{1-6}$alkoxy,
   (4) $C_{1-6}$alkylthio,
   (5) CN,
   (6) $CF_3$,
   (7) $C_{1-6}$alkyl,
   (8) $N_3$,
   (9) —$CO_2H$,
   (10) —$CO_2$—$C_{1-4}$alkyl,
   (11) —$C(R^5)(R^6)$—OH,
   (12) —$C(R^5)(R^6)$—O—$C_{1-4}$alkyl, and
   (13) —$C_{1-6}$alkyl—$CO_2$—$R^5$;

$R^5$, $R^{5'}$ and $R^6$ are each independently selected from the group consisting of
(a) hydrogen,
(b) $C_{1-6}$alkyl,
or $R^5$ and $R^6$ together with the carbon to which they are attached form a saturated monocyclic carbon ring of 3, 4, 5, 6 or 7 atoms.

For purposes of this specification alkyl is defined to include linear, branched, and cyclic structures, with $C_{1-6}$alkyl including methyl, ethyl, propyl, 2-propyl, s- and t-butyl, butyl, pentyl, hexyl, 1,1-dimethylethyl, cyclopropyl, cyclobutyl, cyclopentyl and cyclohexyl. Similarly, C1–6alkoxy is intended to include alkoxy groups of from 1 to 6 carbon atoms of a straight, branched, or cyclic configuration. Examples of lower alkoxy groups include methoxy, ethoxy, propoxy, isopropoxy, cyclopropyloxy, cyclohexyloxy, and the like. Likewise, $C_{1-6}$alkylthio is intended to include alkylthio groups of from 1 to 6 carbon atoms of a straight, branched or cyclic configuration. Examples of lower alkylthio groups include methylthio, propylthio, isopropylthio, cycloheptylthio, etc. By way of illustration, the propylthio group signifies —$SCH_2CH_2CH_3$.

Heteroaryl includes furan, thiophene, pyrrole, isoxazole, isothiazole, pyrazole, oxazole, thiazole, imidazole, 1,2,3-oxadiazole, 1,2,3-thiadiazole, 1,2,3-triazole, 1,3,4- oxadiazole, 1,3,4-thiadiazole, 1,3,4-triazole, 1,2,5-oxadiazole, 1,2,5-thiadiazole, pyridine, pyridazine, pyrimidine, pyrazine, 1,2,4-triazine, 1,3,5-triazine, 1,2,4,5-tetrazine, and the like.

Benzoheteroaryl includes the above heteroaryl rings to which it is possible to fuse a benzene ring.

Exemplifying the invention are:

(a) 3-(4-(Aminosulfonyl)phenyl)-2-(4-fluorophenyl)-5-(2-hydroxy-2-propyl)thiophene, (b) 3-(4-(Aminosulfonyl)phenyl)-2-(4-fluorophenyl) thiophene, (c) 3-(4-(Aminosulfonyl)phenyl)-2-(4-fluorophenyl)-5-(2-propyl)thiophene, (d) 3-(4-(Aminosulfonyl)phenyl)-2-cyclohexylthiophene, (e) 5-(4-Carboxyphenyl)-4-(4-(methylsulfonyl)phenyl) thiophene-2-carboxylic acid, (f) 4-(4-Fluorophenyl)-2-methyl-5-(4-(methylsulfonyl) phenyl)thiazole, (g) 2-(4-Fluorophenyl)-3-(4-(methylsulfonyl)phenyl)-2-cyclopenten-1-one (h) 4-(4-(Methylsulfonyl)phenyl)-5-(4-fluorophenyl)-isothiazole, (i) 3-(4-Fluorophenyl)-4-(4-(methylsulfonyl)phenyl)-2-(5H)-furanone, (j) 3-(4-Fluorophenyl)-4-(4-(aminosulfonyl)phenyl)-2-(5H)-furanone, (k) 3-($^4$-Fluorophenyl)-4-(4-(methylsulfonyl)phenyl) furan, (l) 5,5-Dimethyl-3-(4-fluorophenyl)-4-(4-methylsulfonyl)phenyl)-2-(5H)-furanone, (m) 2-(4-(Aminosulfonyl)phenyl)-3-(4-fluorophenyl) thiophene, and (n) 3-(4-(Trifluoroacetylaminosulfonyl)phenyl)-2-(4-fluorophenyl)thiophene, (o) 3-(3-Fluorophenyl)-4-(4-(methylsulfonyl)phenyl)-2-(5H)-furanone, (p) 5,5-Dimethyl-3-(3-fluorophenyl)-4-(4-methylsulfonyl)phenyl)-2-(5H)-furanone, (q) 5,5-Dimethyl-3-(3-chlorophenyl)-4-(4-methylsulfonyl)phenyl)-2-(5H)-furanone, (r) 3-(3,4-Difluorophenyl)-4-(4-(methylsulfonyl)phenyl)-2-(5H)-furanone, (s) 3-(3,4-Dichlorophenyl)-4-(4-(methylsulfonyl) phenyl)-2-(5H)-furanone, (t) 5,5-Dimethyl-3-(3,4-difluorophenyl)-4-(4-methylsulfonyl)phenyl)-2-(5H)-furanone, (u) 5,5-Dimethyl-3-(3,4-dichlorophenyl)-4-(4-methylsulfonyl)phenyl)-2-(5H)-furanone, (v) 5,5-Dimethyl-3-(4-chlorophenyl)-4-(4-methylsulfonyl)phenyl)-2-(5H)-furanone, (w) 3 -(2-Naphyhyl)-4-(4-(methylsulfonyl)phenyl)-2-(5H)-furanone, (x) 5,5-Dimethyl-3-(2-naphyhyl)-4-(4-(methylsulfonyl) phenyl)-b 2-(5H)-furanone, (y) 3-phenyl-4-(4-(methylsulfonyl)phenyl)-2-(5H)-furanone.

Some of the compounds described herein contain one or more asymmetric centers and may thus give rise to diastereomers and optical isomers. The present invention is meant to comprehend such possible diastereomers as well as their racemic and resolved, enantiomerically pure forms and pharmaceutically acceptable salts thereof.

Some of the compounds described herein contain olefinic double bonds, and unless specified otherwise, are meant to include both E and Z geometric isomers.

In a second embodiment, the invention encompasses pharmaceutical compositions for inhibiting cyclooxygenase and for treating cyclooxygenase mediated diseases as disclosed herein comprising a pharmaceutically acceptable carrier and a non-toxic therapeutically effective amount of compound of formula I as described above.

Within this embodiment the invention encompasses pharmaceutical compositions for inhibiting cyclooxygenase-2 and for treating cyclooxygenase-2 mediated diseases as disclosed herein comprising a pharmaceutically acceptable carrier and a non-toxic therapeutically effective amount of compound of formula I as described above.

In a third embodiment, the invention encompasses a method of inhibiting cyclooxygenase and treating cyclooxygenase mediated diseases, advantageously treated by an active agent that selectively inhibits COX-2 in preference to COX-1 as disclosed herein comprising: administration to a patient in need of such treatment of a non-toxic therapeutically effective amount of a compound of Formula I as disclosed herein.

For purposes of this specification a compound is said to selectively inhibit COX-2 in preference to COX-1 if the ratio of the IC50 concentration for COX-1 inhibition to COX-2 inhibition is 100 or greater.

The pharmaceutical compositions of the present invention comprise a compound of Formula I as an active ingredient or a pharmaceutically acceptable salt, thereof, and may also contain a pharmaceutically acceptable carrier and optionally other therapeutic ingredients. The term "pharmaceutically acceptable salts" refers to salts prepared from pharmaceutically acceptable non-toxic bases including inorganic bases and organic bases. Salts derived from inorganic bases include aluminum, ammonium, calcium, copper, ferric, ferrous, lithium, magnesium, manganic salts, manganous, potassium, sodium, zinc, and the like. Particularly preferred are the ammonium, calcium, magnesium, potassium, and sodium salts. Salts derived from pharmaceutically acceptable organic non-toxic bases include salts of primary, secondary, and tertiary amines, substituted amines including naturally occurring substituted amines, cyclic amines, and basic ion exchange resins, such as arginine, betaine, caffeine, choline, N,N-dibenzylethylenediamnine, diethylamnine, 2-diethylaminoethanol, 2-dimethylaminoethanol, ethanolarnine, ethylenediamine, N-ethylmorpholine, N-ethylpiperidine, glucamine, glucosamine, histidine, hydrabamine, isopropylamine, lysine, methylglucamine, morpholine, piperazine, piperidine, polyamine resins, procaine, purines, theobromine, triethylamine, trimethylamine, tripropylamine, tromethamine, and the like.

It will be understood that in the discussion of methods of treatment which follows, references to the compounds of Formula I are meant to also include the pharmaceutically acceptable salts.

The Compound of Formula I is useful for the relief of pain, fever and inflammation of a variety of conditions including rheumatic fever, symptoms associated with influenza or other viral infections, common cold, low back and neck pain, dysmenorrhea, headache, toothache, sprains and strains, myositis, neuralgia, synovitis, arthritis, including rheumatoid arthritis degenerative joint diseases (osteoarthritis), gout and ankylosing spondylitis, bursitis, burns, injuries, following surgical and dental procedures. In addition, such a compound may inhibit cellular neoplastic transformations and metastic tumor growth and hence can be used in the treatment of cancer. Compounds of formula I may also be useful for the treatment of dementia including pre-senile and senile dementia, and in particular, dementia associated with Alzheimer Disease (ie Alzheimer's dementia).

Compounds of formula I will also be useful in the treatment of Stroke, cerebral ischemia and de-myelinating disorders.

Compounds of formula I will also inhibit prostanoid-induced smooth muscle contraction by preventing the synthesis of contractile prostanoids and hence may be of use in the treatment of dysmenorrhea, premature labor and asthma.

By virtue of its high cyclooxygenase-2 (COX-2) activity and/or its selectivity for cyclooxygenase-2 over cyclooxygenase-1 (COX-1) as defined above, compounds of formula I will prove useful as an alternative to conventional non-steroidal antiinflammatory drugs (NSAID'S) particularly where such non-steroidal antiinflammatory drugs may be contra-indicated such as in patients with peptic ulcers, gastritis, regional enteritis, ulcerative colitis, diverticulitis or with a recurrent history of gastrointestinal lesions; GI bleeding, coagulation disorders including anemia such as hypoprothrombinemia, haemophilia or other bleeding problems (including those relating to reduced or impaired platelet function); kidney disease (eg impaired renal function); those prior to surgery or taking anticoagulants; and those susceptable to NSAID induced asthma.

Similarly, compounds of formula I, will be useful as a partial or complete substitute for conventional NSAID'S in preparations wherein they are presently co-administered with other agents or ingredients. Thus in further aspects, the invention encompasses pharmaceutical compositions for treating cyclooxygenase-2 mediated diseases as defined above comprising a non-toxic therapeutically effective amount of the compound of Formula I as defined above and one or more ingredients such as another pain reliever including acetominophen or phenacetin; a potentiator including caffeine; an H2-antagonist, aluminum or magnesium hydroxide, simethicone, a decongestant including phenylephrine, phenylpropanolamine, pseudoephedrine, oxymetazoline, ephinephrine, naphazoline, xylometazoline, propylhexedrine, or levo-desoxyephedrine; an antiitussive including codeine, hydrocodone, caramiphen, carbetapentane, or dextramethorphan; a diuretic; a sedating or non-sedating antihistamine. In addition the invention encompasses a method of treating cyclooxygenase mediated diseases comprising: administration to a patient in need of such treatment a non-toxic therapeutically effect amount of the compound of Formula I, optionally co-administered with one or more ofsuch ingredients as listed immediately above.

Compounds of the present invention are inhibitors of cyclooxygenase-2 and are thereby useful in the treatment of cyclooxygenase-2 mediated diseases as enumerated above. This activity is illustrated by their ability to selectively inhibit cyclooxygenase-2 over cyclooxygenase-1. Accordingly, in one assay, the ability of the compounds of this invention to treat cyclooxygenase mediated diseases can be demonstrated by measuring the amount of prostaglandin $E_2$ ($PGE_2$) synthesized in the presence of arachidonic acid, cyclooxygenase-1 or cyclooxygenase-2 and a compound of formula I. The IC50 values represent the concentration of inhibitor required to return $PGE_2$ synthesis to 50% of that obtained as compared to the uninhibited control. Illustrating this aspect, we have found that the Compounds of the Examples are more than 100 times more effective in inhibiting COX-2 than they are at inhibiting COX-1. In addition they all have a COX-2 IC50 of 1 nM to 1 mM. By way of comparison, Ibuprofen has an IC50 for COX-2 of 1 mM, and Indomethacin has an IC50 for COX-2 of approximately 100 nM. For the treatment of any of these cyclooxygenase mediated diseases, compounds of formula I may be administered orally, topically, parenterally, by inhalation spray or rectally in dosage unit formulations containing conventional non-toxic pharmaceutically acceptable carriers, adjuvants and vehicles. The term parenteral as used herein includes subcutaneous injections, intravenous, intramuscular, intrastemal injection or infusion techniques. In addition to the treatment of warm-blooded animals such as mice, rats, horses, cattle sheep, dogs, cats, etc., the compound of the invention is effective in the treatment of humans.

As indicated above, pharmaceutical compositions for treating cyclooxygenase-2 mediated diseases as defined may optionally include one or more ingredients as listed above.

The pharmaceutical compositions containing the active ingredient may be in a form suitable for oral use, for example, as tablets, troches, lozenges, aqueous or oily suspensions, dispersible powders or granules, emulsions, hard or soft capsules, or syrups or elixirs. Compositions intended for oral use may be prepared according to any method known to the art for the manufacture of pharmaceutical compositions and such compositions may contain one or more agents selected from the group consisting of sweetening agents, flavoring agents, coloring agents and preserving agents in order to provide pharmaceutically elegant and palatable preparations. Tablets contain the active ingredient in admixture with non-toxic pharmaceutically acceptable excipients which are suitable for the manufacture of tablets. These excipients may be for example, inert diluents, such as calcium carbonate, sodium carbonate, lactose, calcium phosphate or sodium phosphate; granulating and disintegrating agents, for example, corn starch, or alginic acid; binding agents, for example starch, gelatin or acacia, and lubricating agents, for example, magnesium stearate, stearic acid or talc. The tablets may be uncoated or they may be coated by known techniques to delay disintegration and absorption in the gastrointestinal tract and thereby provide a sustained action over a longer period. For example, a time delay material such as glyceryl monostearate or glyceryl distearate may be employed. They may also be coated by the technique described in the U.S. Pat. Nos. 4,256,108; 4,166,452; and 4,265,874 to form osmotic therapeutic tablets for control release.

Formulations for oral use may also be presented as hard gelatin capsules wherein the active ingredient is mixed with an inert solid diluent, for example, calcium carbonate, calcium phosphate or kaolin, or as soft gelatin capsules wherein the active ingredients is mixed with water or an oil medium, for example peanut oil, liquid paraffin, or olive oil.

Aqueous suspensions contain the active material in admixture with excipients suitable for the manufacture of aqueous suspensions. Such excipients are suspending agents, for example sodium carboxymethyl-cellulose, methylcellulose, hydroxy-propylmethycellulose, sodium alginate, polyvinyl-pyrrolidone, gum tragacanth and gum acacia; dispersing or wetting agents may be a naturally-occurring phosphatide, for example lecithin, or condensation products of an alkylene oxide with fatty acids, for example polyoxyethylene stearate, or condensation products of ethylene oxide with long chain aliphatic alcohols, for example heptadecaethylene-oxycetanol, or condensation products of ethylene oxide with partial esters derived from fatty acids and a hexitol such as polyoxyethylene sorbitol monooleate, or condensation products of ethylene oxide with partial esters derived from fatty acids and hexitol anhydrides, for example polyethylene sorbitan monooleate. The aqueous suspensions may also contain one or more preservatives, for example ethyl, or n-propyl, p-hydroxybenzoate, one or more coloring agents, one or more flavoring agents, and one or more sweetening agents, such as sucrose, saccharin or aspartame.

Oily suspensions may be formulated by suspending the active ingredient in a vegetable oil, for example arachis oil, olive oil, sesame oil or coconut oil, or in mineral oil such as liquid paraffin. The oily suspensions may contain a thickening agent, for example beeswax, hard paraffin or cetyl alcohol. Sweetening agents such as those set forth above, and flavoring agents may be added to provide a palatable oral preparation. These compositions may be preserved by the addition of an anti-oxidant such as ascorbic acid.

Dispersible powders and granules suitable for preparation of an aqueous suspension by the addition of water provide the active ingredient in admixture with a dispersing or wetting agent, suspending agent and one or more preservatives. Suitable dispersing or wetting agents and suspending agents are exemplified by those already mentioned above. Additional excipients, for example sweetening, flavoring and coloring agents, may also be present.

The pharmaceutical compositions of the invention may also be in the form of an oil-in-water emulsions. The oily phase may be a vegetable oil, for example olive oil or arachis oil, or a mineral oil, for example liquid paraffin or mixtures of these. Suitable emulsifying agents may be naturally-occurring phosphatides, for example soy bean, lecithin, and esters or partial esters derived from fatty acids and hexitol anhydrides, for example sorbitan monooleate, and condensation products of the said partial esters with ethylene oxide, for example polyoxyethylene sorbitan monooleate. The emulsions may also contain sweetening and flavouring agents.

Syrups and elixirs may be formulated with sweetening agents, for example glycerol, propylene glycol, sorbitol or sucrose. Such formulations may also contain a demulcent, a preservative and flavoring and coloring agents. The pharmaceutical compositions may be in the form of a sterile injectable aqueous or oleagenous suspension. This suspension may be formulated according to the known art using those suitable dispersing or wetting agents and suspending agents which have been mentioned above. The sterile injectable preparation may also be a sterile injectable solution or suspension in a non-toxic parenterally-acceptable diluent or solvent, for example as a solution in 1,3-butane diol. Among the acceptable vehicles and solvents that may be employed are water, Ringer's solution and isotonic sodium chloride solution. In addition, sterile, fixed oils are conventionally employed as a solvent or suspending medium. For this purpose any bland fixed oil may be employed including synthetic mono- or diglycerides. In addition, fatty acids such as oleic acid find use in the preparation of injectables.

Compounds of formula I may also be administered in the form of a suppositories for rectal administration of the drug. These compositions can be prepared by mixing the drug with a suitable non-irritating excipient which is solid at ordinary temperatures but liquid at the rectal temperature and will therefore melt in the rectum to release the drug. Such materials are cocoa butter and polyethylene glycols.

For topical use, creams, ointments, jellies, solutions or suspensions, etc:, containing the compound of Formula I are employed. (For purposes of this application, topical application shall include mouth washes and gargles.)

Dosage levels of the order of from about 0.01 mg to about 140 mg/kg of body weight per day are useful in the treatment of the above-indicated conditions, or alternatively about 0.5 mg to about 7 g per patient per day. For example, inflammation may be effectively treated by the administration of from about 0.01 to 50 mg of the compound per kilogram of body weight per day, or alternatively about 0.5 mg to about 3.5 g per patient per day.

The amount of active ingredient that may be combined with the carrier materials to produce a single dosage form will vary depending upon the host treated and the particular mode of administration. For example, a formulation intended for the oral administration of humans may contain from 0.5 mg to 5 g of active agent compounded with an appropriate and convenient amount of carrier material which may vary from about 5 to about 95 percent of the total composition. Dosage unit forms will generally contain between from about 1 mg to about 500 mg of an active ingredient, typically 25 mg, 50 mg, 100 mg, 200 mg, 300 mg, 400 mg, 500 mg, 600 mg, 800 mg, or 1000 mg.

It will be understood, however, that the specific dose level for any particular patient will depend upon a variety of factors including the age, body weight, general health, sex, diet, time of administration, route of administration, rate of excretion, drug combination and the severity of the particular disease undergoing therapy.

The present invention provides a method of treating a neurodegenerative disease and in particular Alzheimers disease which comprises administering to a human in need thereof a therapeutically effective amount of a non-steroid COX-II inhibitor.

From another aspect this invention provides the use of a COX-II inhibitor in the manufacture of a medicament for the treatment of neurodegenerative diseases including dementia, and in particular Alzheimers disease. Risk factors include those based on Apo lipoprotein genotype, age, Mild Cognitive Impairment and family History.

When used herein the term "treating" includes treatment of existing disease and prophylactic treatment of those at risk of developing the disease.

When used herein the term "COX-II" inhibitor means a compound able to inhibit human COX-II enzyme without causing relatively significant inhibition of human COX-I enzyme. Generally compounds which bind at least 10 times as well to COX-I receptors as to COX-II receptors (ie will have a $IC_{50}$ COX-II receptor only one tenth the numerical value of the COX-I receptor) are chosen for use in the invention, more aptly 20 times as well, favourably 50 times as well most favourably at least 100 times as well, and preferably at least 10.00 times as well.

The COX-II inhibitors for use in this invention are most aptly those which are highly brain penetrant so that the maximum concentration of COX-II inhibitor after administration of the anti-neurodegenerative for example the anti-alzheimer effective dose of COX-II inhibitor is at least the binding $IC_{50}$ value and preferably at least 10 times that value for example at least 100 times the binding $IC_{50}$ value.

The COX-II inhibitor may be of any structural type other than a steroid. However, most aptly the COX-II inhibitor employed in this invention is not a carboxylic acid or a salt thereof. Most favourably it will possess a $SO_2CH_3$, $NHSO_2CH_3$, $SO_2NH_2$, $SO_2CHCH_3$ or like substituent on an aromatic ring especially on a phenyl ring.

Our investigations and statements made in the more recent of the following patents indicate that COX-II inhibitors may be found in U.S. Pat. Nos 4,375,479; 4,590,205; 4,820,827; 5,343,991; EP 0418845; WO 91/19708; WO 94/15932 and WO 94/13635. Each of the above documents is incorporated herein by cross reference.

Thus in one aspect this invention provides a method of treating a neurodegenerative disease and in particular Alzheimers disease which comprises administering to a patient therapeutically effective amount of a compound generically disclosed (and preferably a compound specifically described) in U.S. Pat. Nos. 4,375,479; 4,590,205; 4,820,827; 5,344,991; EP 0418845; WO 91/19708; WO 94/15932 or WO 94/13635 all of which are incorporated herein by cross reference.

The invention also provides the use of such compounds in the manufacture of a medicament for the treatment of neurodegenerative disease and in particular Alzheimers disease.

Favourably the COX-II inhibitor employed is one described in WO 94/26731 (published Nov. 24, 1994), WO 94/20480 (published Sep. 15, 1994), U.S. Pat. No. 5,436,265 (issued Jul. 25, 1995), WO 95/00501 (published Jan. 5, 1995) or WO 95/18799 (published Jul. 13, 1995) all of which are incorporated herein by cross reference.

The medicaments for treating neurodegenerative disease may be formulated as described in the aforementioned referenced documents. The medicament may be employed in the doses and regimens set out in the aforementioned referenced documents with respect to the treatment of diseases which benefit from the administration of a COX-II inhibitor.

It is a great advantage of this invention that treatment may be carried out without causing gastric side effects of the type that can occur when COX I inhibitors are used for prolonged periods. Since neurodegenerative diseases such as Alzheimers disease are generally progressive treatment may need to take place for a number of years. Thus the provision of medicaments which are surprisingly effective without any significant tendency to cause gastric side effects at the therapeutic dose is of great use particularly to the elderly. The use of medicaments of this invention for the treatment of patients who are asymptotic is also envisaged especially in those cases where genetic information suggests that the patient is likely to develop Alzheimers disease or other neurodegenerative disease especially those which may be termed dementia, for example senile dementia or pre-senile dementia.

Favourably this invention provides a method of treating neurodegenerative disease without any significant tendency to cause gastric side effects which comprises the oral administration of a pharmaceutical composition which comprises an effective amount of a COX-II inhibitor and a pharmaceutical acceptable carrier therefor.

Such a method is applicable to patients with overt symptoms of disease and is applicable without overt symptoms of the disease (asymptotic patients).

Generally the oral dosage form will be administered from 1 to 6 times per day. Preferably the oral dosage form will be administered once or twice per day.

EXAMPLE

Using PCR analysis of MRNA extracted from the post-mortem hippocampus of 7 AD patients and 6 age-matched control patients (with no history of neurological or neuropsychiatric diseases, we found COX-II MRNA in 6 AD patients. Four of the control patients showed no COX-II mRNA. In situ hybridization histochemistry also showed COX-II mRNA in the hippocampus of 4 AD patients but not in 5 control patients. Western blot analysis of temporal lobe cortex showed COX-II protein in 3AD patients but not in 3 control patients.

These results show that COX-II is induced in the medial temporal lobe of AD patients, a brain region most severely affected during alzheimers disease process. The results indicate that the inflammatory condition associated with AD involve COX-1 in its aetiology and show that treating AD patients with brain penetrant selective COX-il inhibitors will be effective.

Methods of Synthesis

The compounds of the present invention can be prepared according to the following methods.

Method A:

The b-chlorovinylaldehyde III can be obtained from the ketone II and the Vilsmeier reagent (DMF-POCl$_3$) using the general method described by Weissenfels (Z. Chem. 1966, 6, 471). The thiophene compound IV is obtained from III using the general method described by Weissenfels (Z. Chem., 1973, 13, 57). The thiol compound V can be obtained after oxidation of compound IV (R$^a$=SMe) with one equivalent of m-CPBA followed by treatment of the resulting sulfoxide with TFAA at reflux. The sulfonamide group (VI) can then be formed by the method of Kharash (J. Amer. Chem. Soc. 1951, 73, 3240). The hydrolysis of compound VI and decarboxylation with Cu bronze in quinoline provides compound VII. Compound VII (R$^4$=H) can be treated with halogenating agent such as bromine in acetic acid to allow the preparation of the 5-bromothiophene (VII, R$^4$=Br). When it is desired to have a nitrile group at C-5, this can be accomplished from VI via amide formation using the Weinreb methodology (Tetrahedron Letters, 1977, 4171) followed by dehydration with TFAA. The CF$_3$ group can be introduced at C-5 of VII via the method of Girard (J. Org. Chem. 1983, 48, 3220).

The introduction of an alkyl group at C-5 can be achieved via a Friedel-Crafts reaction on VII (R$^4$=H) and an acyl chloride, Cl—CO—lower alkyl and a catalyst such as TiCl$_4$, followed by reduction. For R$^4$=Me, this can be achieved from the ester (R$^4$=CO$_2$Me) via a DIBAL-H reduction followed by deoxygenation using the method of Lau (J. Org. Chem. 1986, 51, 3038). Tertiary alcohols (R$^4$=C(CH$_3$)$_2$OH) can be obtained from VI and MeMgBr. These tertiary alcohols can also be deoxygenated using the method of Lau. Similarly, the thiophene IX can be prepared from ketone VIII.

METHOD A

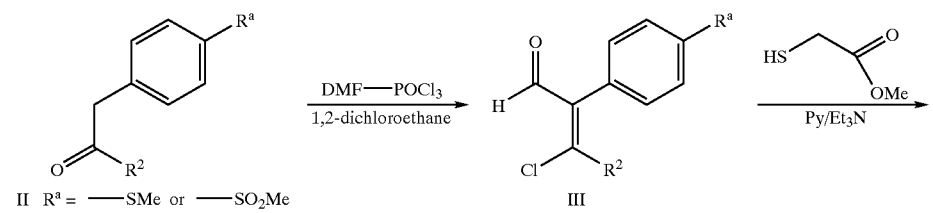

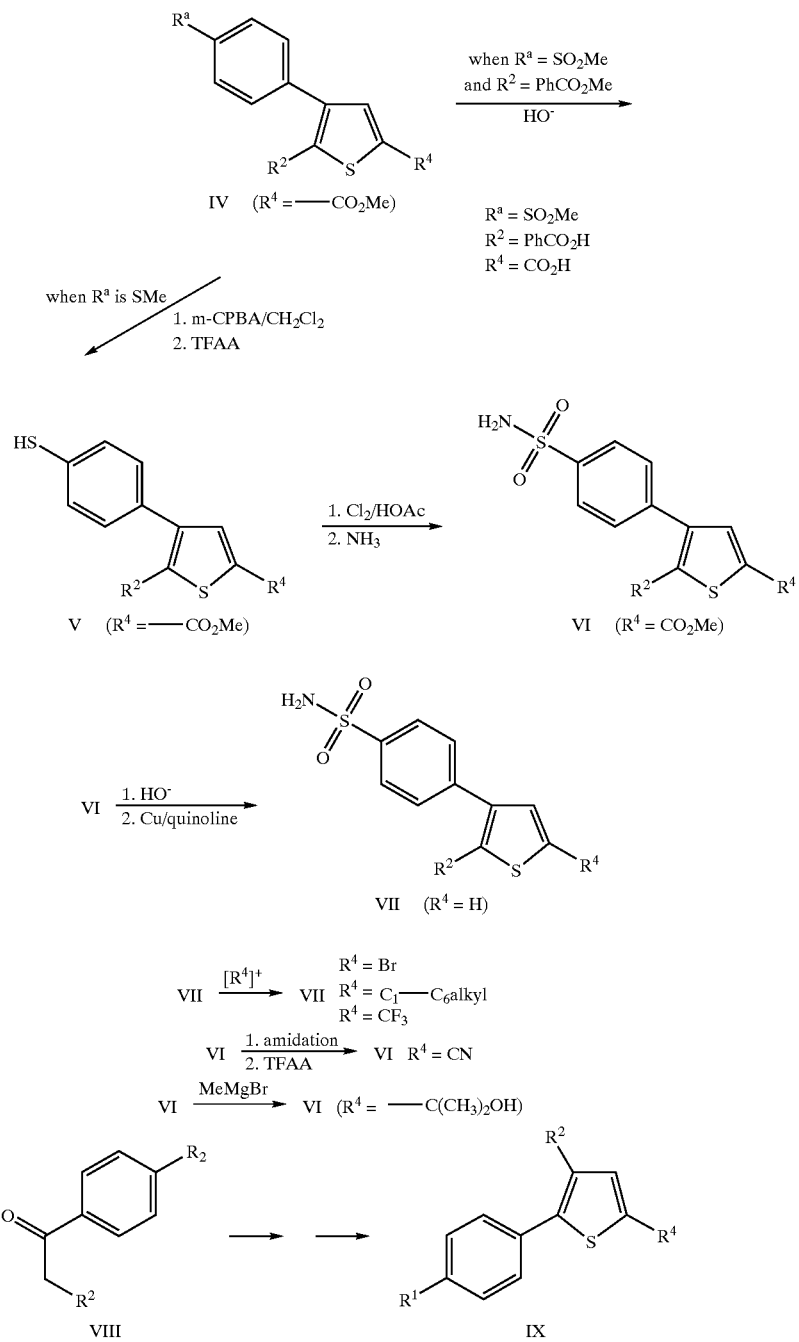
Method B:
Ketone X can be converted to the thiophene compound XI using general methods already described in Method A. The thiophene XII can be prepared by metallation of XI with n-BuLi, quenching with methyl phosphonic dichloride and addition of water or ammonia (X'=OH or $NH_2$). Similarly, the other regioisomer XIV can be prepared from ketone XIII.
METHOD B
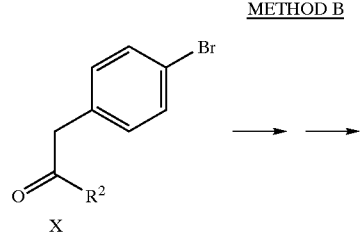

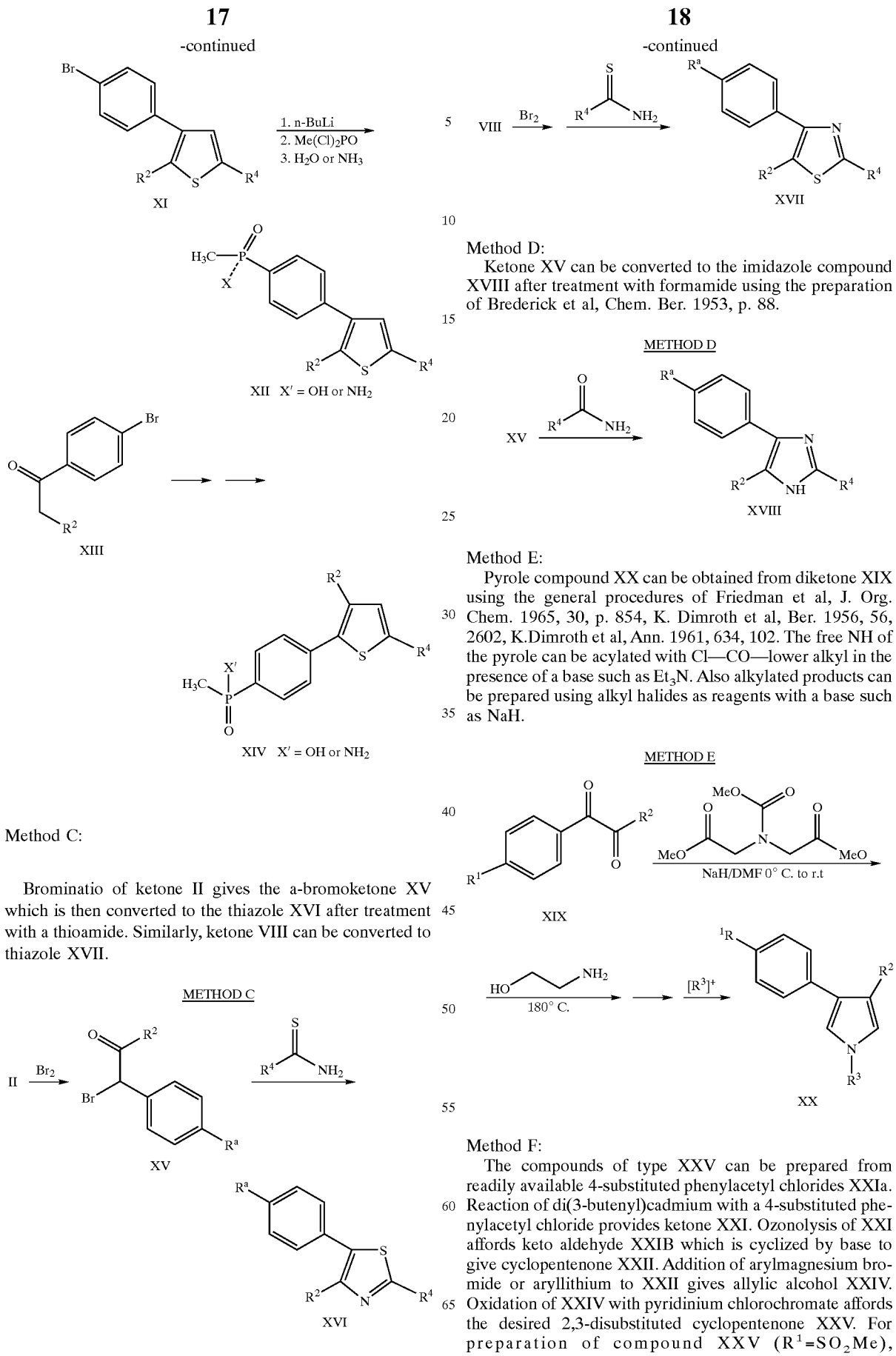

Method C:

Brominatio of ketone II gives the a-bromoketone XV which is then converted to the thiazole XVI after treatment with a thioamide. Similarly, ketone VIII can be converted to thiazole XVII.

Method D:

Ketone XV can be converted to the imidazole compound XVIII after treatment with formamide using the preparation of Brederick et al, Chem. Ber. 1953, p. 88.

Method E:

Pyrole compound XX can be obtained from diketone XIX using the general procedures of Friedman et al, J. Org. Chem. 1965, 30, p. 854, K. Dimroth et al, Ber. 1956, 56, 2602, K.Dimroth et al, Ann. 1961, 634, 102. The free NH of the pyrole can be acylated with Cl—CO—lower alkyl in the presence of a base such as $Et_3N$. Also alkylated products can be prepared using alkyl halides as reagents with a base such as NaH.

Method F:

The compounds of type XXV can be prepared from readily available 4-substituted phenylacetyl chlorides XXIa. Reaction of di(3-butenyl)cadmium with a 4-substituted phenylacetyl chloride provides ketone XXI. Ozonolysis of XXI affords keto aldehyde XXIB which is cyclized by base to give cyclopentenone XXII. Addition of arylmagnesium bromide or aryllithium to XXII gives allylic alcohol XXIV. Oxidation of XXIV with pyridinium chlorochromate affords the desired 2,3-disubstituted cyclopentenone XXV. For preparation of compound XXV ($R^1=SO_2Me$), 4-methylthiophenyllithium is used followed by oxidation with the magesium salt of monoperoxyphthalic acid (MMPP) or m-chloroperoxybenzoic acid (mCPBA) to introduce the required methylsulfonyl group in XXV.

METHOD F

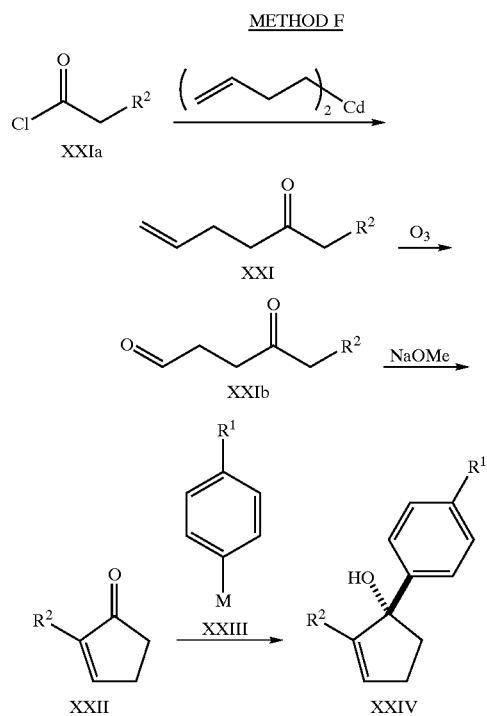

Method G:

The sequence of Method G is the same as in Method F except $R^1$ containing acid chloride is used as starting material. $R^2$ is introduced at a later stage via a carbonyl addition reaction, followed by PCC oxidation.

METHOD G

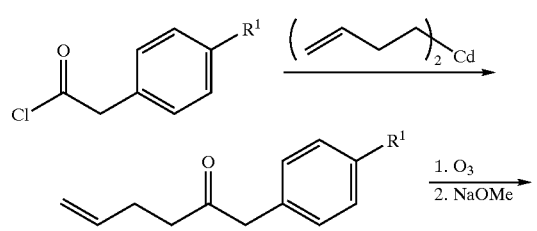

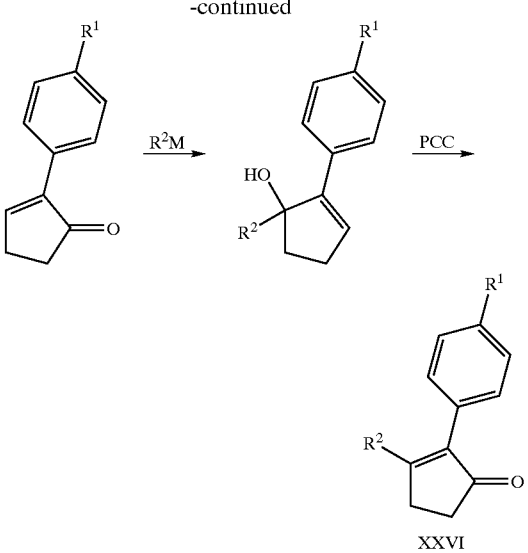

Method H:

The 4,5-disubstituted isothiazoles and isothiazol-3(2H)-one-1,1-dioxides can be prepared by the general method described by B. Schulze et al, Helvetica Chimica Acta, 1991, 74, 1059. Thus, aldehyde III ($R^a$=SO$_2$Me) or XXVII is treated with excess NH$_4$SCN in refluxing acetone to provide the corresponding 4,5-disubstituted isothiazoles XXX and XXVIII, oxidation of which with hydrogen peroxide yields XXXI and XXIX.

METHOD H

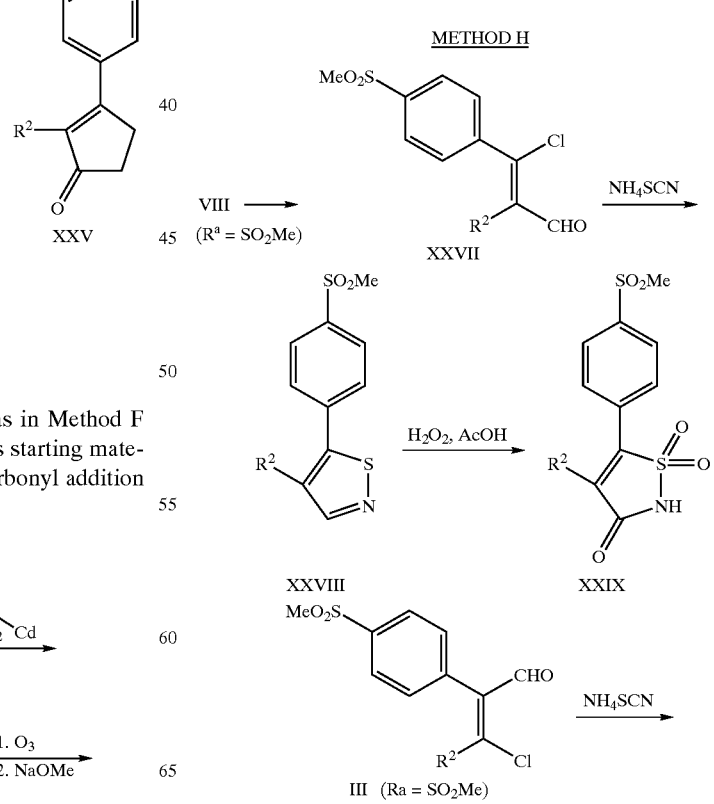

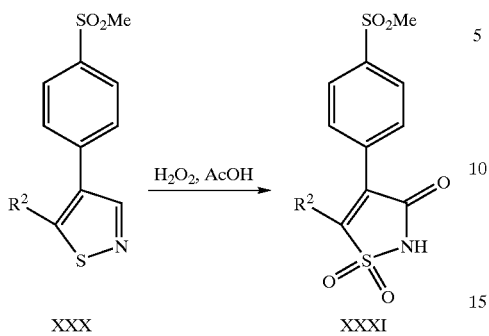

XXX → XXXI (H₂O₂, AcOH)

METHOD J

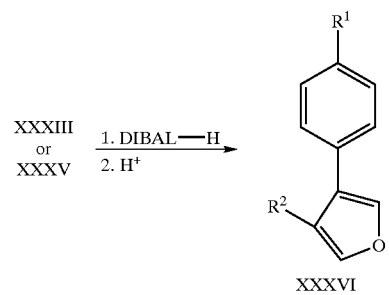

XXXIII or XXXV → XXXVI (1. DIBAL—H, 2. H⁺)

Method I:

An appropriately substituted aryl bromomethyl ketone is reacted with an appropriately substituted aryl acetic acid in a solvent such as acetonitrile in the presence of a base such as triethylamine and then treated with 1,8-diazabicyclo[5.4.0]undec-7-ene (DBU) to afford either the lactone XXXIII or XXXV.

Method K:

The preparation of lactams XXXVII and XXXIX can be achieved by the same reaction as described in Method I, except an appropriate amide is used.

METHOD I

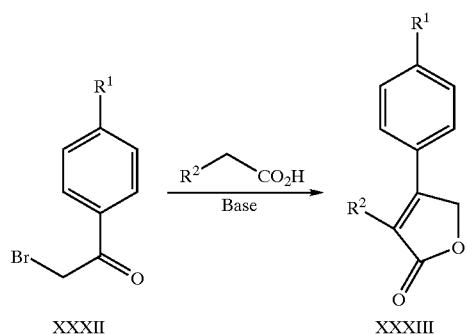

XXXII → XXXIII

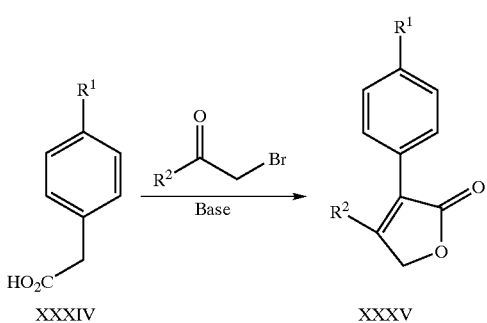

XXXIV → XXXV (R² is a mono- or disubstituted phenyl or a mono- or disubstituted heteroaryl)

METHOD K

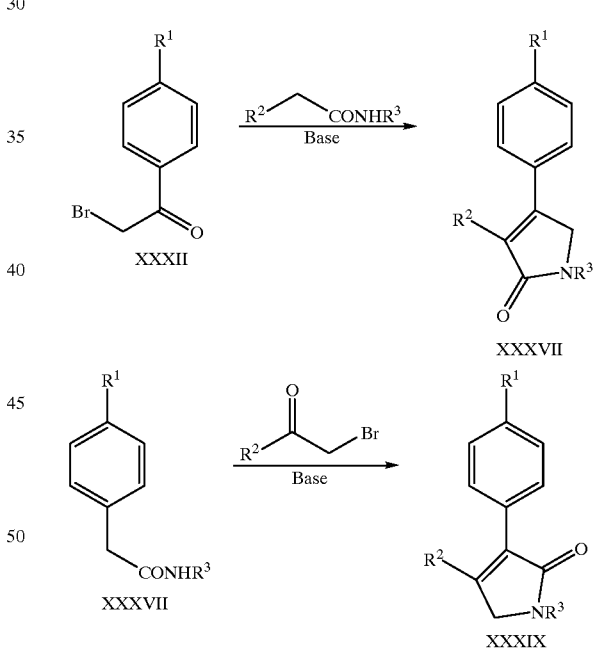

XXXII → XXXVII

XXXVII → XXXIX

Method J:

Either of the lactones XXXIII or XXXV in a solvent such as THF is reacted with a reducing agent such as diisobutyl aluminium hydride or lithium borohydride at −78° C., to yield the furan XXXVI.

Method L:

Methyl 2-hydroxy isobutyrate is silylated with TMSCl to give the TMS ether XXXXI, which is treated with 4-methylthiophenyllithium to provide ketone XI. Desilylation followed by acylation yields keto-ester XXXXIV, which can be cyclized to lactone XXXXV by base catalysis. Oxidation of XXV with MMPP or mCPBA affords the desired product XXXXVI.

METHOD L

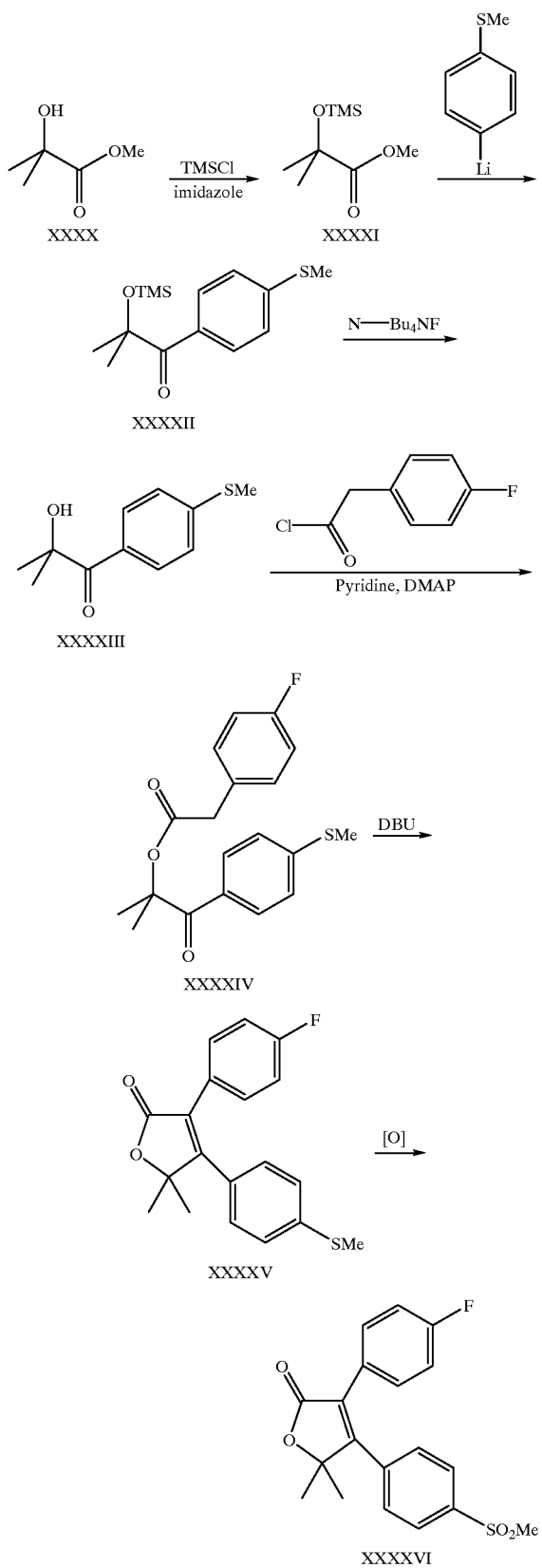

METHOD M

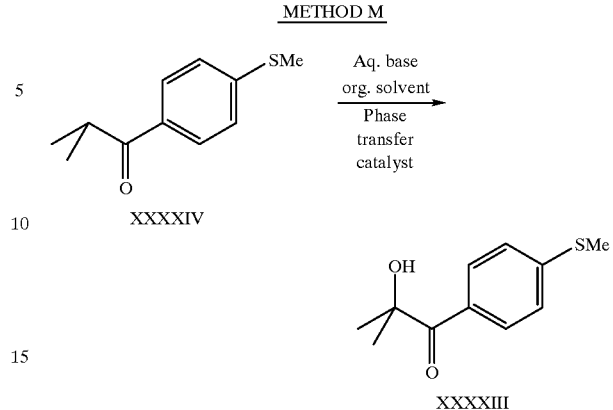

An alternative preparation of the hydroxy ketone XXXXII is the oxidation of the known (J. Org. Chem. 1991 56, 5955-8; Sulfur Lett. 1991, 12, 123-32) ketone XXXXIV. A mixture of XXXXIV, aquous base, such as NaOH, organic solvents such as carbon tetrachloride/toluene and a phase transfer catalyst such as ALIQUAT 336 is stirred in air at room temperature to provide XXXXIII. Compound XXXXIII is also described in U.S. Pat. No. 4,321,118 and Org. Coat. 1986, 6, 175-95.

Representative Compounds

Tables I and II illustrate compounds of formula I.

TABLE I

| | Example | Method |
|---|---|---|
| (structure: thiophene with 4-SO₂NH₂-phenyl, 4-F-phenyl, and C(CH₃)₂OH substituents) | 1 | A |
| (structure: thiophene with 4-SO₂NH₂-phenyl and 4-F-phenyl substituents) | 2 | A |
| (structure: thiophene with 4-SO₂NH₂-phenyl, 4-F-phenyl, and CH(Me)₂ substituents) | 3 | A |

TABLE I-continued

| Structure | Example | Method |
|---|---|---|
| 2-cyclohexyl-3-(4-sulfamoylphenyl)thiophene | 4 | A |
| 4-(4-methylsulfonylphenyl)-5-(4-carboxyphenyl)thiophene-2-carboxylic acid | 5 | A |
| 2-methyl-4-(4-fluorophenyl)-5-(4-methylsulfonylphenyl)thiazole | 6 | C |
| 2-(4-fluorophenyl)-3-(4-methylsulfonylphenyl)cyclopent-2-enone | 7 | F |
| 5-(4-fluorophenyl)-4-(4-methylsulfonylphenyl)isothiazole | 8 | H |
| 3-(4-fluorophenyl)-4-(4-methylsulfonylphenyl)-2(5H)-furanone | 9 | I |
| 3-(4-fluorophenyl)-4-(4-sulfamoylphenyl)-2(5H)-furanone | 10 | I |
| 3-(4-fluorophenyl)-4-(4-methylsulfonylphenyl)furan | 11 | J |
| 3-(4-fluorophenyl)-4-(4-methylsulfonylphenyl)-5,5-dimethyl-2(5H)-furanone | 12 | L |
| 3-(4-fluorophenyl)-2-(4-sulfamoylphenyl)thiophene | 13 | A |

TABLE I-continued

| Structure | Example | Method |
|---|---|---|
| 3-(4-(SO₂NHC(O)CF₃)phenyl)-2-(4-fluorophenyl)thiophene | 14 | A |
| 3-(2,4-difluorophenyl)-4-(4-(methylsulfonyl)phenyl)-2(5H)-furanone | 15 | I |
| 3-(3,4-difluorophenyl)-4-(4-(methylsulfonyl)phenyl)-2(5H)-furanone | 16 | I |
| 3-(2,6-difluorophenyl)-4-(4-(methylsulfonyl)phenyl)-2(5H)-furanone | 17 | I |
| 3-(2,5-difluorophenyl)-4-(4-(methylsulfonyl)phenyl)-2(5H)-furanone | 18 | I |
| 3-(3,5-difluorophenyl)-4-(4-(methylsulfonyl)phenyl)-2(5H)-furanone | 19 | I |
| 3-(4-bromophenyl)-4-(4-(methylsulfonyl)phenyl)-2(5H)-furanone | 20 | I |
| 3-(4-chlorophenyl)-4-(4-(methylsulfonyl)phenyl)-2(5H)-furanone | 21 | I |
| 3-(4-methoxyphenyl)-4-(4-(methylsulfonyl)phenyl)-2(5H)-furanone | 22 | I |
| 3-phenyl-4-(4-(methylsulfonyl)phenyl)-2(5H)-furanone | 23 | I |

TABLE I-continued
| | Example | Method |
|---|---|---|
| 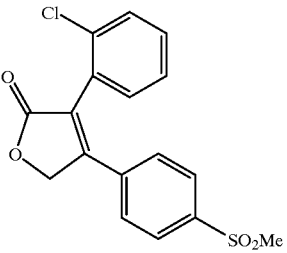 | 24 | I |
| 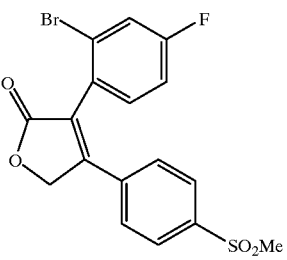 | 25 | I |
| 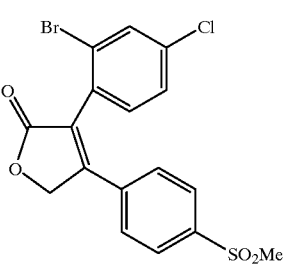 | 26 | I |
| 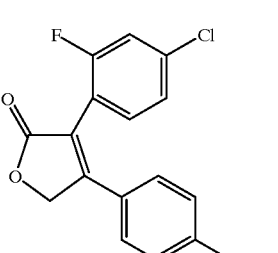 | 27 | I |
| 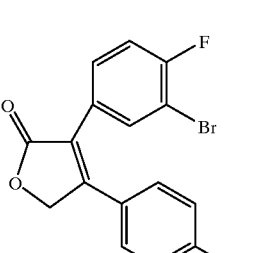 | 28 | I |
| 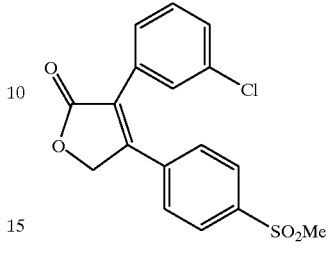 | 29 | I |
| 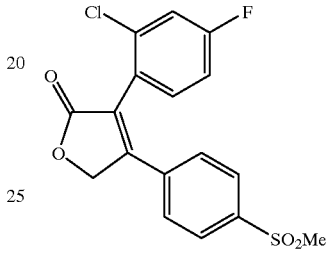 | 30 | I |
| 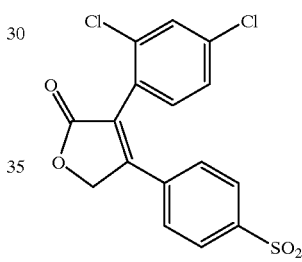 | 31 | I |
| 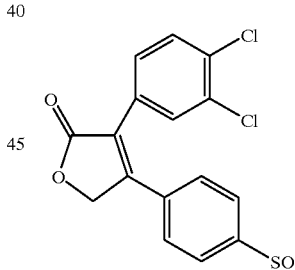 | 32 | I |
| 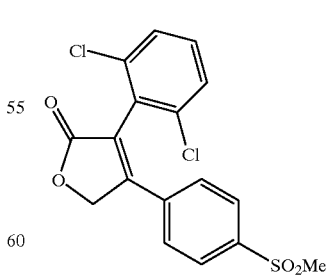 | 33 | I |

TABLE I-continued

| Structure | Example | Method |
|---|---|---|
| 3-(3-chloro-4-fluorophenyl)-4-(4-methylsulfonylphenyl)furan-2(5H)-one | 34 | I |
| 3-(4-trifluoromethylphenyl)-4-(4-methylsulfonylphenyl)furan-2(5H)-one | 35 | I |
| 3-(3-fluoro-4-methoxyphenyl)-4-(4-methylsulfonylphenyl)furan-2(5H)-one | 36 | I |
| 3-(3-chloro-4-methoxyphenyl)-4-(4-methylsulfonylphenyl)furan-2(5H)-one | 37 | I |
| 3-(3-bromo-4-methoxyphenyl)-4-(4-methylsulfonylphenyl)furan-2(5H)-one | 38 | I |
| 3-(2-fluorophenyl)-4-(4-methylsulfonylphenyl)furan-2(5H)-one | 39 | I |
| 3-(4-methylthiophenyl)-4-(4-methylsulfonylphenyl)furan-2(5H)-one | 40 | I |
| 3-(3-fluorophenyl)-4-(4-methylsulfonylphenyl)furan-2(5H)-one | 41 | I |
| 3-(2-chloro-6-fluorophenyl)-4-(4-methylsulfonylphenyl)furan-2(5H)-one | 42 | I |
| 3-(3-bromo-4-methylphenyl)-4-(4-methylsulfonylphenyl)furan-2(5H)-one | 43 | I |

TABLE I-continued
| | Example | Method |
|---|---|---|
| 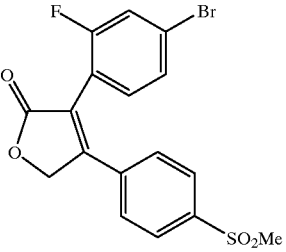 | 44 | I |
| 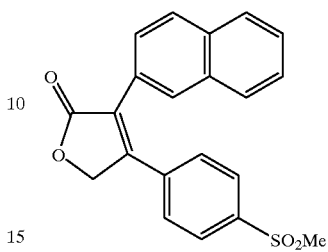 | 45 | I |
| 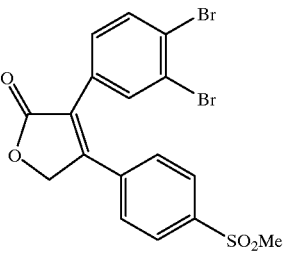 | 46 | I |
| 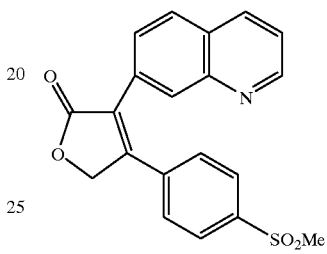 | 47 | I |
| 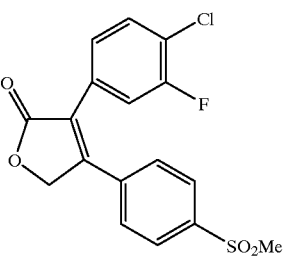 | 48 | I |
TABLE I-continued
| | Example | Method |
|---|---|---|
| 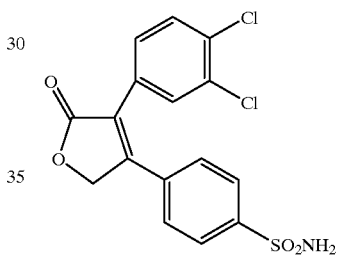 | 49 | I |
| 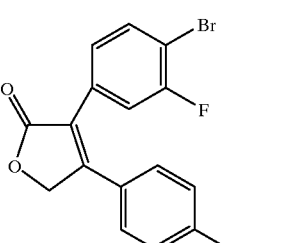 | 50 | I |
| 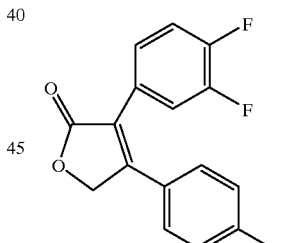 | 51 | I |
| 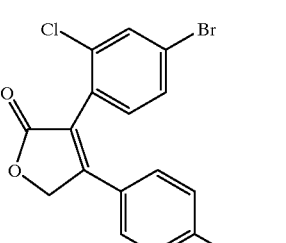 | 52 | I |
| 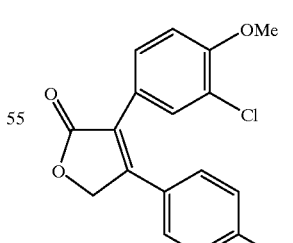 | 53 | I |

TABLE I-continued
| | Example | Method |
|---|---|---|
| 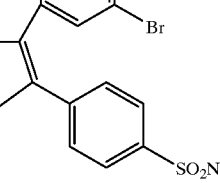 | 54 | I |
| 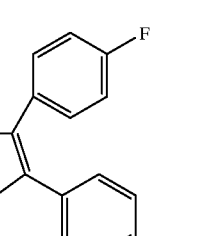 | 55 | H |
| 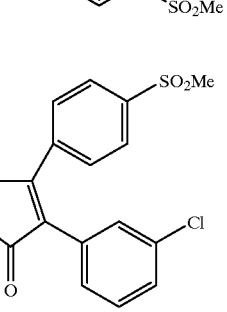 | 56 | L + M |
| 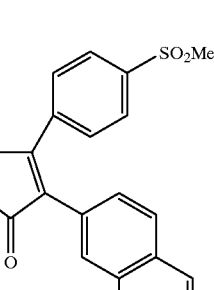 | 57 | L + M |
| 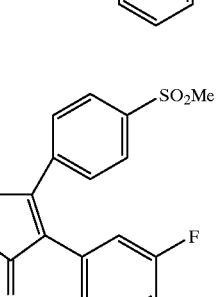 | 58 | L + M |
TABLE I-continued
| | Example | Method |
|---|---|---|
| | 59 | L + M |
| | 60 | L + M |
TABLE II TABLE II-continued
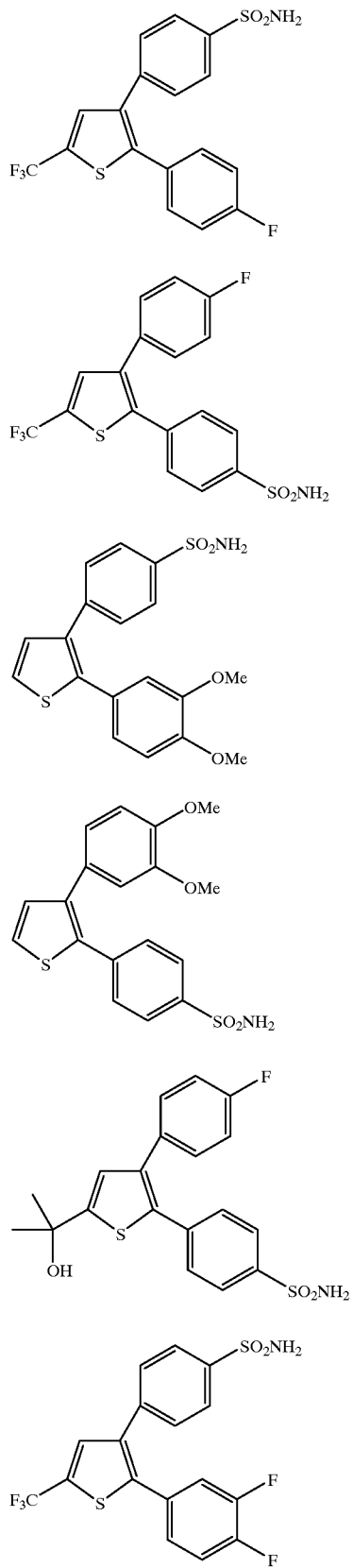
TABLE II-continued
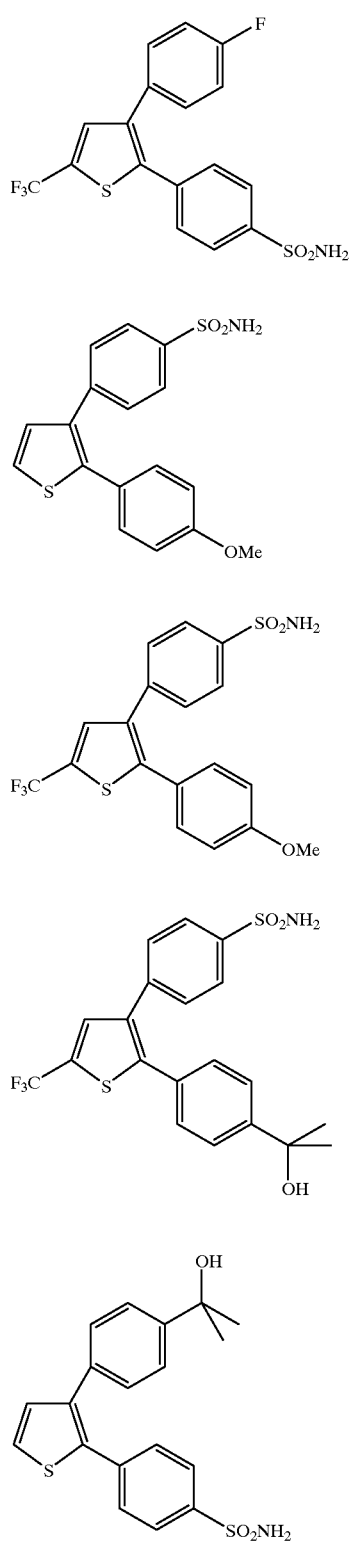

TABLE II-continued
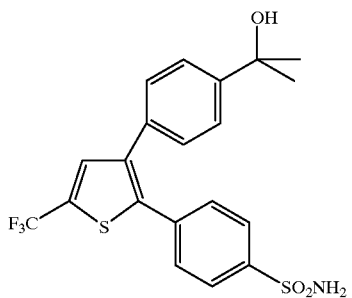
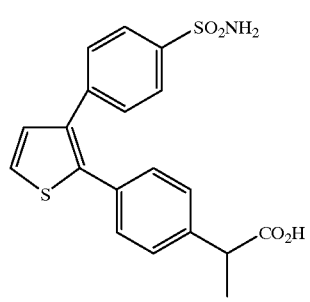
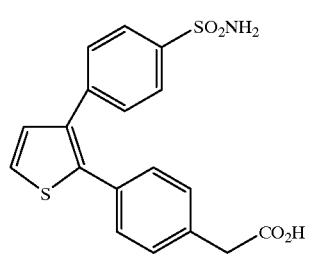
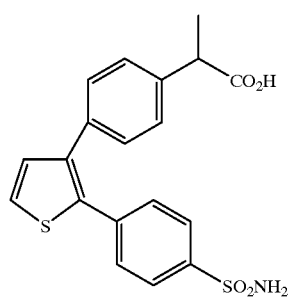
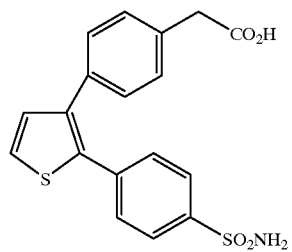
TABLE II-continued
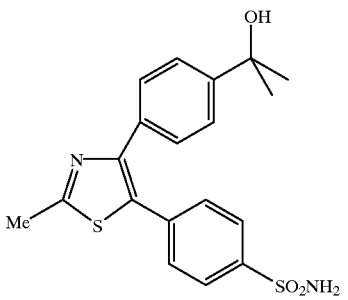
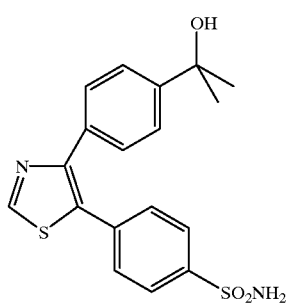
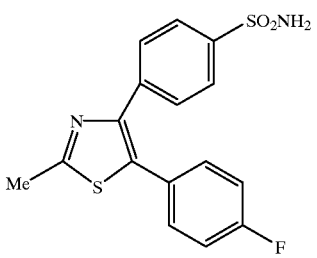
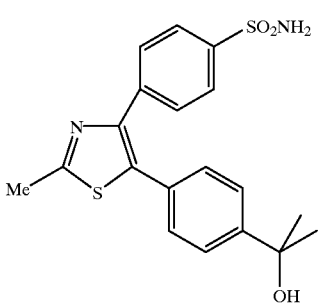
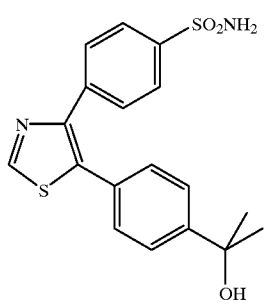

TABLE II-continued
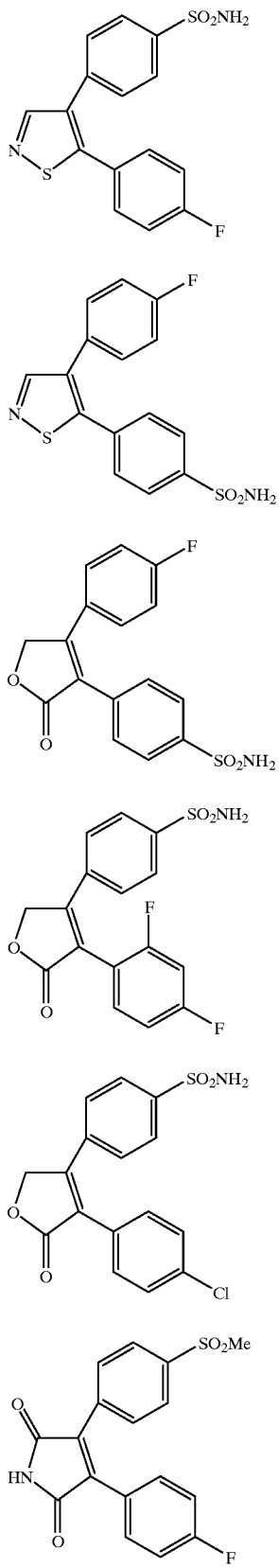
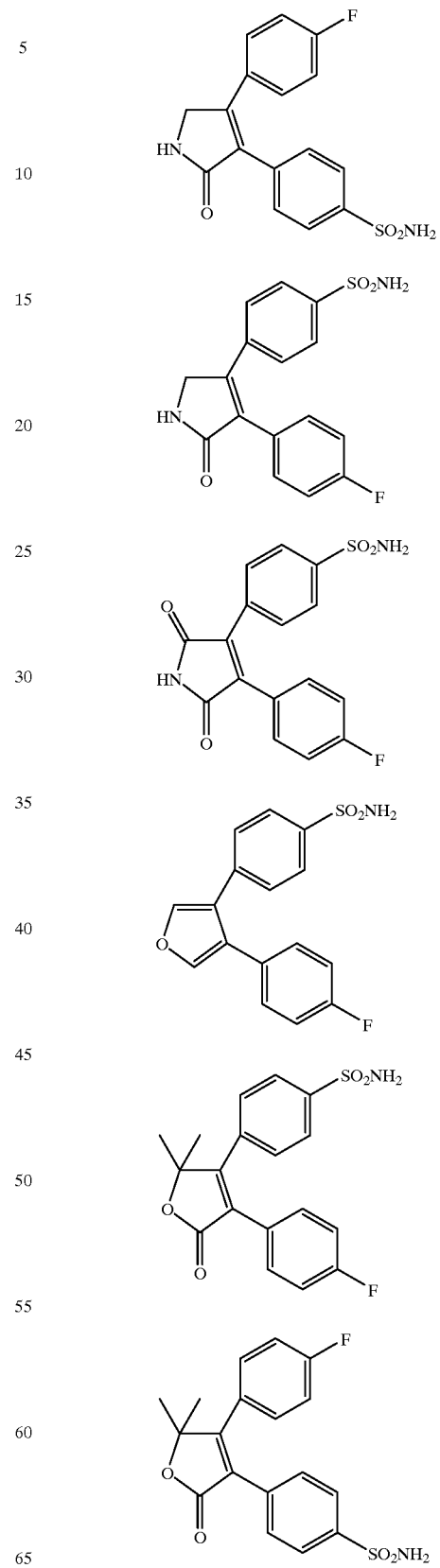

TABLE II-continued
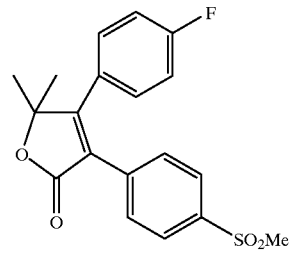
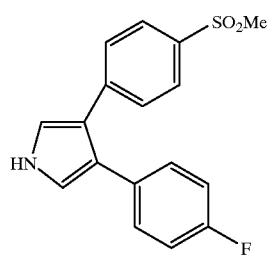
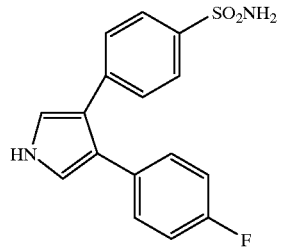
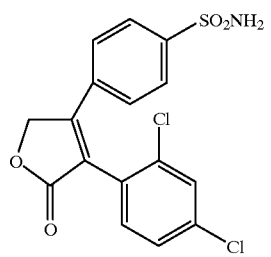
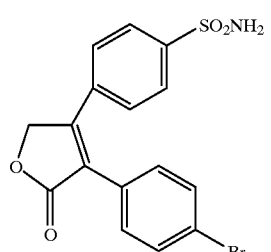
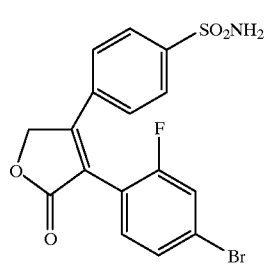
TABLE II-continued
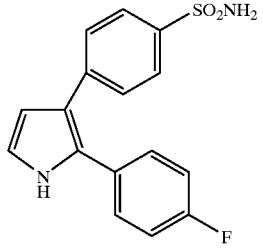
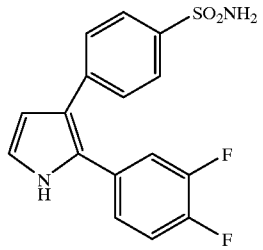
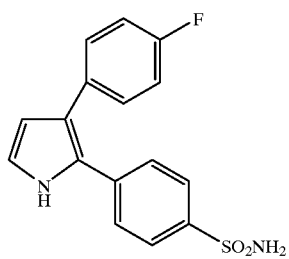
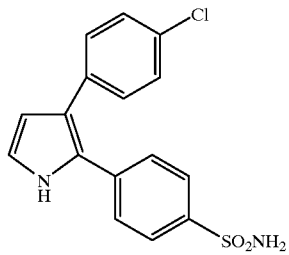
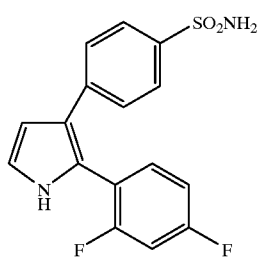
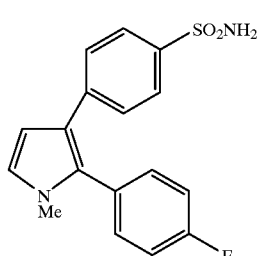

TABLE II-continued
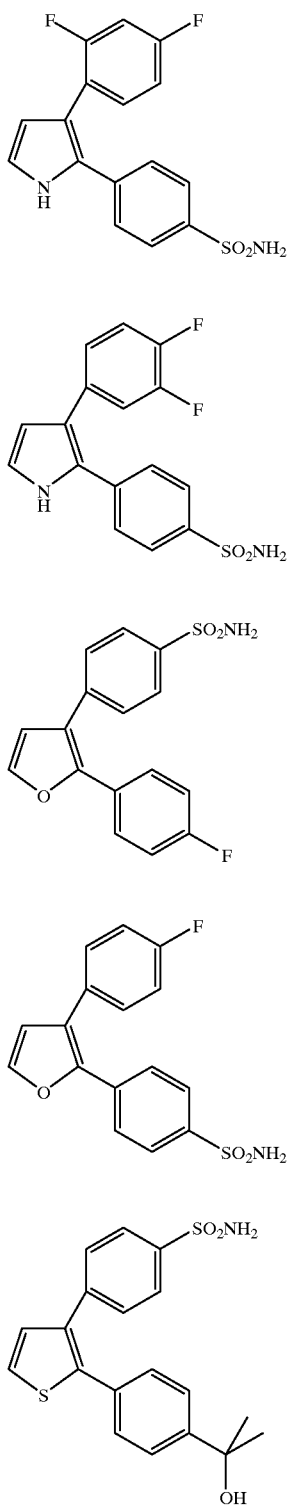
TABLE II-continued
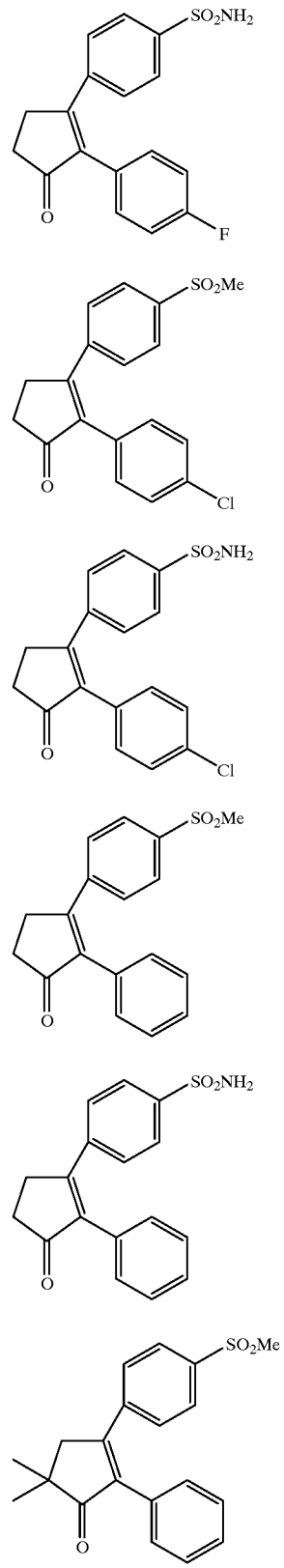

TABLE II-continued
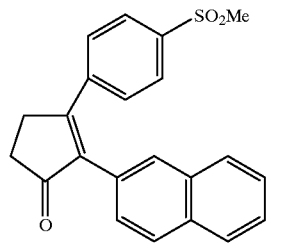
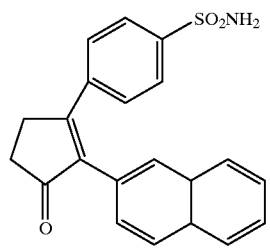
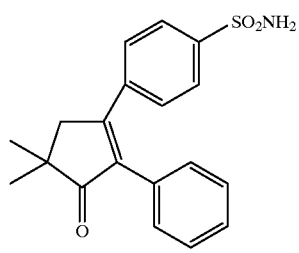
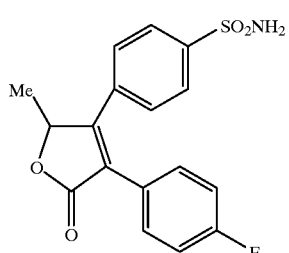
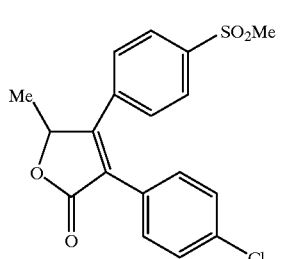
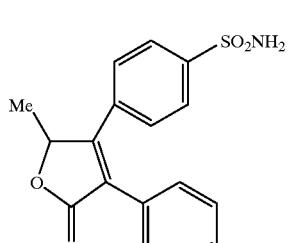
TABLE II-continued
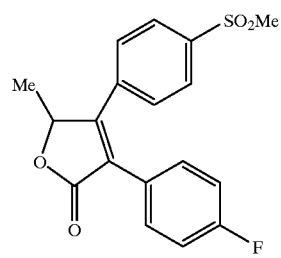
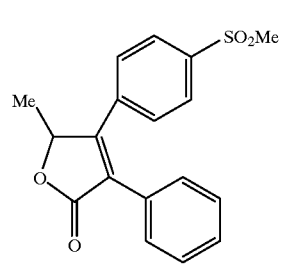
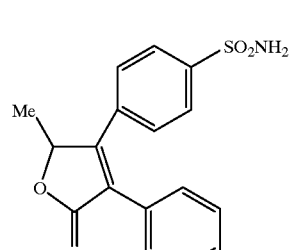
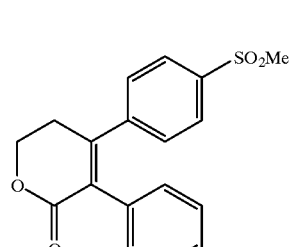
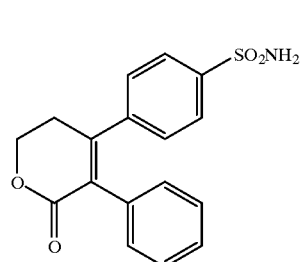
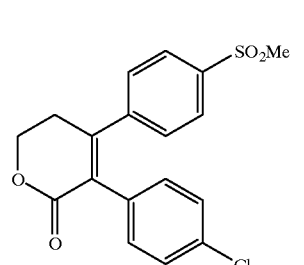

TABLE II-continued
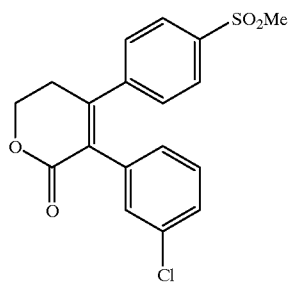
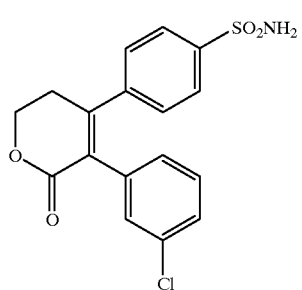
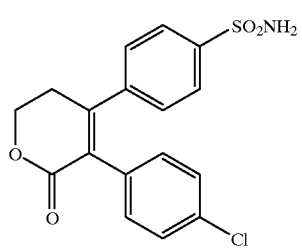
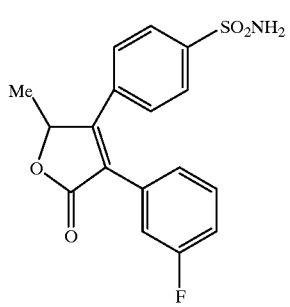
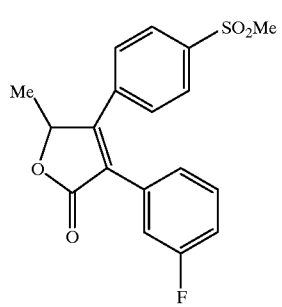
TABLE II-continued
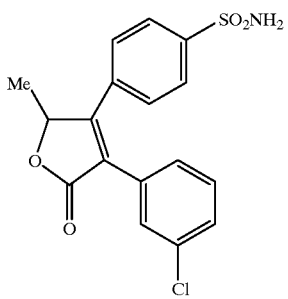
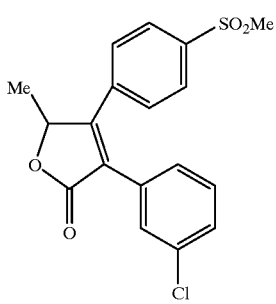
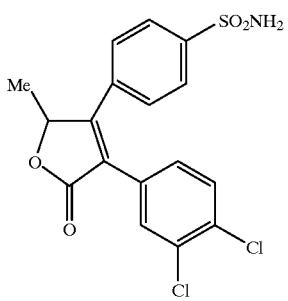
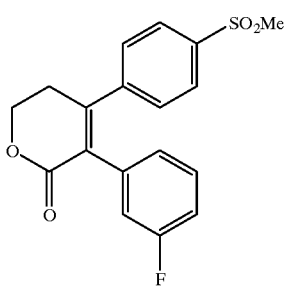

TABLE II-continued
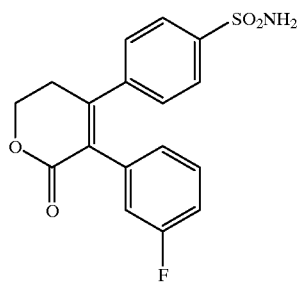
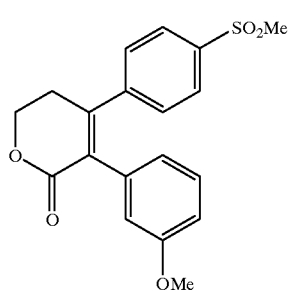
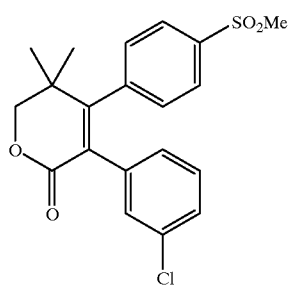
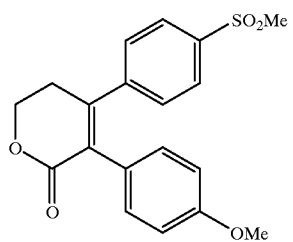
TABLE II-continued
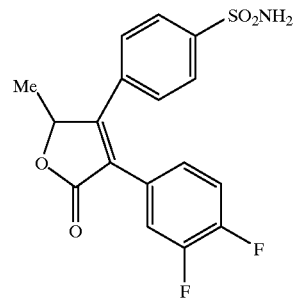
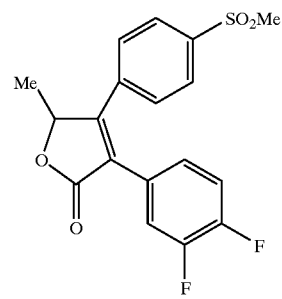
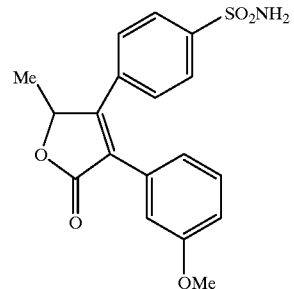
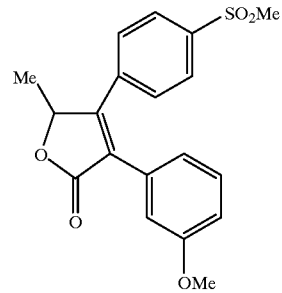
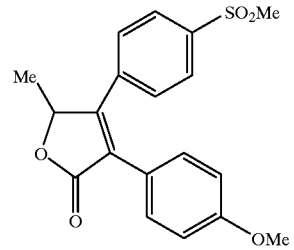

TABLE II-continued

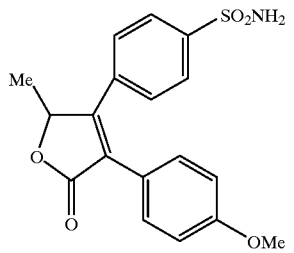

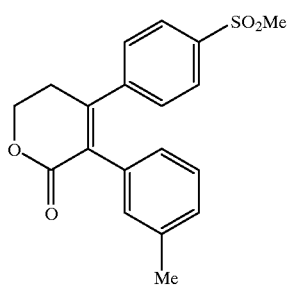

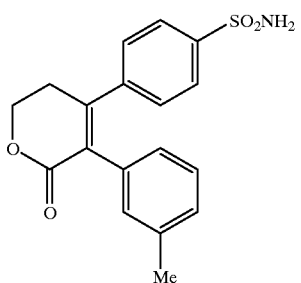

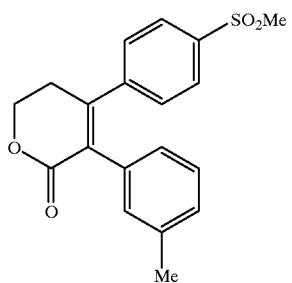

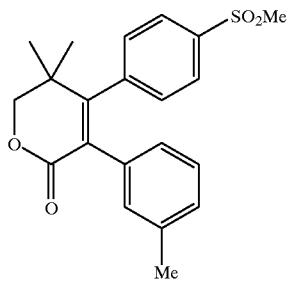

TABLE II-continued

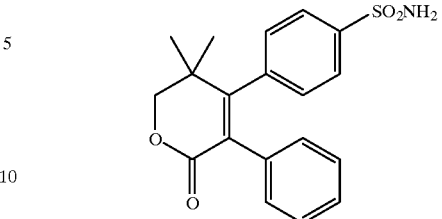

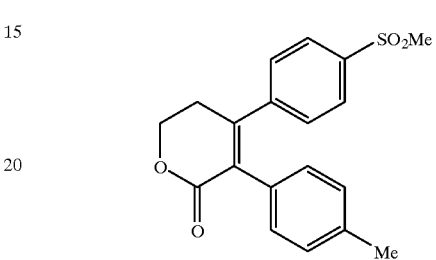

Assays for Determining Biological Activity

The compound of Formula I can be tested using the following assays to determine their cyclooxygenase-2 inhibiting activity.

Inhibition of Cyclooxygenase Activity

Compounds were tested as inhibitors of cyclooxygenase activity in whole cell and microsomal cyclooxygenase assays. Both of these assays measured prostaglandin $E_2$ ($PGE_2$) synthesis in response to arachidonic acid, using a radioimmunoassay. Cells used for whole cell assays, and from which microsomes were prepared for microsomal assays, were human osteosarcoma 143 cells (which specifically express cyclooxygenase-2) and human U-937 cells (which specifically express cyclooxygenase-1). In these assays, 100% activity is defined as the difference between prostaglandin $E_2$ synthesis in the absence and presence-of arachidonate addition. $IC_{50}$ values represent the concentration of putative inhibitor required to return $PGE_2$ synthesis to 50% of that obtained as compared to the uninhibited control. Representative results are shown in Table III.

Representative Rat Paw Edema Assay—Protocol

Male Sprague-Dawley rats (150–200g) were fasted overnight and were given po either vehicle (5% tween 80 or 1% methocel) or a test compound at 9–10 am. One hr later, a line was drawn using a permanent marker at the level above the ankle in one hind paw to define the area of the paw to be monitored. The paw volume (Voh) was measured using a plethysmometer (Ugo-Basile, Italy) based on the principle of water displacement. The animals were then injected subplantarly with 50 ul of a 1% carrageenan solution in saline (FMC Corp, Maine) into the paw using an insulin syringe with a 25-gauge needle (i.e. 500 ug carrageenan per paw). Three hr later, the paw volume ($V_{3h}$) was measured and the increases in paw volume ($V_{3h}-V_{Oh}$) were calculated. The animals were euthanized by $CO_2$ aphyxiation and the absence or presence of stomach lesions scored. Stomach scores were expressed as the sum of total lesions in mm. Paw edema data were compared with the vehicle-control group and percent inhibition calculated taking the values in the control group as 100%. Since a maximum of 60–70% inhibition (paw edema) was obtained with standard NSAIDs, ED30 values were used for comparison. All treatment groups were coded to eliminate observer bias. With this protocol, the ED30 for Indomethacin is 1.0 mg/kg. Representative results are shown in Table IV.

TABLE III*

| Example | Whole Cells | | | Microsomes | | |
|---|---|---|---|---|---|---|
| | Conc. (nM) | COX-2 % inhib. | COX-1 % inhib. | Conc. (nM) | COX-2 % inhib. | COX-1 % inhib. |
| 1 | 100 | 96 | 12 | 100 | 53 | 8 |
| 2 | 10 | 69 | 0 | 10 | 49 | 25 |
| 3 | 10 | 42 | | 10 | 33 | 19 |
| 3 | 100 | 100 | | 100 | 76 | 12 |
| 4 | | | | 10 | 47 | 2 |
| 5 | 10 | 0 | 0 | 10 | 43 | 31 |
| 6 | 100 | 78 | | 100 | 19 | 16 |
| 7 | 100 | 74 | 0 | 1000 | 58 | 16 |
| 8 | 10 | 41 | | | | |
| 8 | 100 | 89 | | | | |
| 9 | 100 | 83 | | 100 | 37 | 9 |
| 10 | 100 | 95 | | 100 | 71 | 12 |
| 11 | 100 | 39 | | 100 | 46 | 7 |
| 12 | 100 | 54 | | | | |
| 13 | 10 | 41 | | 10 | 52 | 7 |
| 13 | 100 | 84 | | 10 | 58 | 10 |
| 14 | 10 | 73 | | 10 | 45 | 29 |
| 14 | 100 | 89 | | 100 | 63 | 0 |
| 14 | 1000 | 101 | | 1000 | 69 | 0 |
| 15 | 20 | 39 | | | | |
| 15 | 80 | 76 | | | | |
| 15 | 160 | 95 | | | | |
| 16 | 20 | 41 | | | | |
| 16 | 40 | 50 | | | | |
| 16 | 160 | 85 | | | | |
| 17 | 40 | 41 | | | | |
| 17 | 160 | 77 | | | | |
| 18 | 40 | 24 | | | | |
| 18 | 160 | 58 | | | | |
| 19 | 40 | 21 | | | | |
| 19 | 160 | 59 | | | | |
| 20 | 10 | 70 | | | | |
| 20 | 40 | 91 | | | | |
| 21 | 10 | 50 | | | | |
| 21 | 40 | 94 | | | | |
| 22 | 20 | 39 | | | | |
| 22 | 160 | 98 | | | | |
| 23 | 20 | 50 | | | | |
| 23 | 160 | 88 | | | | |
| 24 | 40 | 43 | | | | |
| 24 | 160 | 78 | | | | |
| 25 | 160 | 40 | | | | |
| 26 | 80 | 27 | | | | |
| 26 | 160 | 39 | | | | |
| 27 | 20 | 38 | | | | |
| 27 | 160 | 97 | | | | |
| 28 | 20 | 48 | | | | |
| 28 | 160 | 69 | | | | |
| 29 | 20 | 78 | | | | |
| 29 | 160 | 85 | | | | |
| 30 | 160 | 30 | | | | |
| 31 | 20 | 49 | | | | |
| 31 | 160 | 87 | | | | |
| 32 | 5 | 43 | | | | |
| 32 | 10 | 73 | | | | |
| 32 | 40 | 92 | | | | |
| 32 | 80 | 99 | | | | |
| 33 | 160 | 6 | | | | |
| 34 | 10 | 30 | | | | |
| 34 | 40 | 80 | | | | |
| 34 | 160 | 102 | | | | |
| 35 | 20 | 32 | | | | |
| 35 | 40 | 57 | | | | |
| 35 | 160 | 83 | | | | |
| 36 | 10 | 11 | | | | |
| 36 | 40 | 50 | | | | |
| 36 | 160 | 89 | | | | |

TABLE III*-continued

| Example | Whole Cells | | | Microsomes | | |
|---|---|---|---|---|---|---|
| | Conc. (nM) | COX-2 % inhib. | COX-1 % inhib. | Conc. (nM) | COX-2 % inhib. | COX-1 % inhib. |
| 37 | 10 | 53 | | | | |
| 37 | 40 | 82 | | | | |
| 37 | 160 | 93 | | | | |
| 38 | 10 | 25 | | | | |
| 38 | 40 | 63 | | | | |
| 38 | 160 | 88 | | | | |
| 39 | 10 | 17 | | | | |
| 39 | 160 | 84 | | | | |
| 40 | 10 | 43 | | | | |
| 40 | 40 | 72 | | | | |
| 40 | 160 | 96 | | | | |
| 41 | | | | | | |
| 41 | | | | | | |
| 42 | 20 | 10 | | | | |
| 42 | 160 | 44 | | | | |
| 43 | 10 | 78 | | | | |
| 43 | 40 | 101 | | | | |
| 44 | 20 | 14 | | | | |
| 44 | 40 | 55 | | | | |
| 44 | 160 | 106 | | | | |
| 45 | 10 | 16 | | | | |
| 45 | 40 | 61 | | | | |
| 45 | 160 | 101 | | | | |
| 46 | 10 | 76 | | | | |
| 46 | 40 | 94 | | | | |
| 46 | 160 | 97 | | | | |
| 47 | 10 | 61 | | | | |
| 47 | 40 | 74 | | | | |
| 47 | 160 | 101 | | | | |
| 48 | 10 | 7 | | | | |
| 48 | 160 | 47 | | | | |
| 49 | 10 | 53 | | | | |
| 49 | 40 | 91 | | | | |
| 49 | 80 | 99 | | | | |
| 50 | 80 | 42 | | | | |
| 51 | 5 | 49 | | | | |
| 51 | 20 | 95 | | | | |
| 51 | 40 | 102 | | | | |
| 52 | 10 | 50 | | | | |
| 52 | 40 | 82 | | | | |
| 52 | 160 | 102 | | | | |
| 53 | 10 | 54 | | | | |
| 53 | 40 | 96 | | | | |
| 53 | 160 | 102 | | | | |
| 54 | 10 | 81 | | | | |
| 54 | 80 | 91 | | | | |
| 54 | 160 | 99 | | | | |
| 55 | 10 | 48 | | | | |
| 55 | 80 | 59 | | | | |
| 55 | 160 | 65 | | | | |

*In the whole cell assay Ibuprofen has an IC50 for COX-1 of 1000 nM, and an IC50 for COX-2 of 3000 nM. Similarly, Indomethacin has an IC50 for COX-1 of 100 nM, and an IC50 for COX-2 of 10 nM.

TABLE IV

| ED30 (mg/kg) | STRUCTURE |
|---|---|
| ~3.00 | 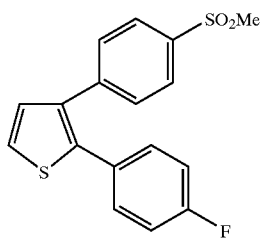 |

TABLE IV-continued

| ED30 (mg/kg) | STRUCTURE |
|---|---|
| >10.00 | 3,4-diaryl thiophene (4-SO2Me-phenyl, 4-F-phenyl) |
| 1.40 | 2,3-diaryl thiophene (3-(4-SO2NH2-phenyl), 2-(4-F-phenyl)) |
| 2.80 (in 1% methocel) 0.72 | 3,4-diaryl furan-2(5H)-one (4-(4-SO2Me-phenyl), 3-(4-F-phenyl)) |
| 0.43 | 2,3-diaryl cyclopentenone (3-(4-SO2Me-phenyl), 2-(4-F-phenyl)) |
| ~3.00 | 2-(4-F-phenyl)-5-(2-hydroxyprop-2-yl)-3-(4-SO2NH2-phenyl)thiophene |
| >3.00 3.00 | 3,4-diaryl thiophene (4-SO2NH2-phenyl, 4-F-phenyl) |

TABLE IV-continued

| ED30 (mg/kg) | STRUCTURE |
|---|---|
| 1.10 | 4,5-diaryl isothiazole (4-(4-SO2Me-phenyl), 5-(4-F-phenyl)) |
| <0.30 | 2,3-diaryl thiophene (3-(4-F-phenyl), 2-(4-SO2NH2-phenyl)) |
| 0.42 | 5,5-dimethyl-3,4-diaryl furan-2(5H)-one (4-(4-SO2Me-phenyl), 3-(4-F-phenyl)) |
| 0.034 | 3,4-diaryl furan-2(5H)-one (4-(4-SO2NH2-phenyl), 3-(4-F-phenyl)) |
| 2.03 | 3,4-diaryl furan-2(5H)-one (4-(4-SO2Me-phenyl), 3-(2,4-difluorophenyl)) |
| 1.49 | 3,4-diaryl furan-2(5H)-one (4-(4-SO2Me-phenyl), 3-(2,6-difluorophenyl)) |

TABLE IV-continued

| ED30 (mg/kg) | STRUCTURE |
|---|---|
| 0.35 | 3-(3,4-difluorophenyl)-4-(4-(methylsulfonyl)phenyl)-2(5H)-furanone |
| 0.33 | 3-(4-bromophenyl)-4-(4-(methylsulfonyl)phenyl)-2(5H)-furanone |
| 0.90 | 3-(4-chlorophenyl)-4-(4-(methylsulfonyl)phenyl)-2(5H)-furanone |
| 0.38 | 4-(4-(methylsulfonyl)phenyl)-3-phenyl-2(5H)-furanone |
| 0.88 | 3-(2-bromo-4-chlorophenyl)-4-(4-(methylsulfonyl)phenyl)-2(5H)-furanone |
| 0.47 | 3-(4-chloro-2-fluorophenyl)-4-(4-(methylsulfonyl)phenyl)-2(5H)-furanone |

TABLE IV-continued

| ED30 (mg/kg) | STRUCTURE |
|---|---|
| 0.71 | 3-(3-chlorophenyl)-4-(4-(methylsulfonyl)phenyl)-2(5H)-furanone |
| ~1.00 | 3-(3-bromo-4-fluorophenyl)-4-(4-(methylsulfonyl)phenyl)-2(5H)-furanone |
| 1.85 | 3-(2,4-dichlorophenyl)-4-(4-(methylsulfonyl)phenyl)-2(5H)-furanone |
| 0.22<br>0.23 | 3-(3,4-dichlorophenyl)-4-(4-(methylsulfonyl)phenyl)-2(5H)-furanone |
| 0.43 | 3-(3-chloro-4-fluorophenyl)-4-(4-(methylsulfonyl)phenyl)-2(5H)-furanone |
| 2.17 | 4-(4-(methylsulfonyl)phenyl)-3-(4-(trifluoromethyl)phenyl)-2(5H)-furanone |

TABLE IV-continued
| ED30 (mg/kg) | STRUCTURE |
|---|---|
| 0.81 | 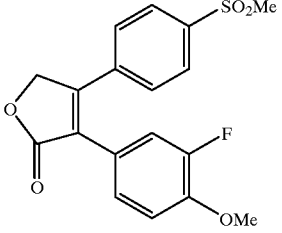 |
| 0.68 | 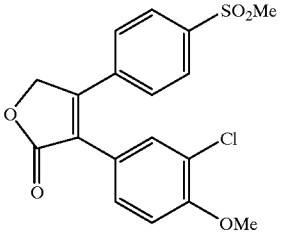 |
| 0.16 | 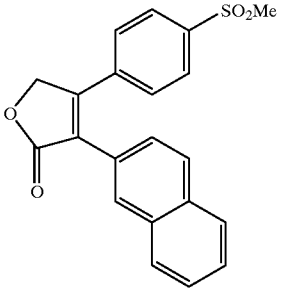 |
| ~1.00 | 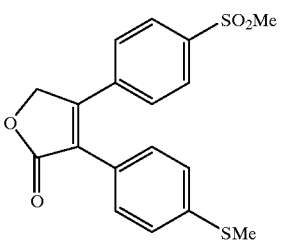 |
| 0.33 | 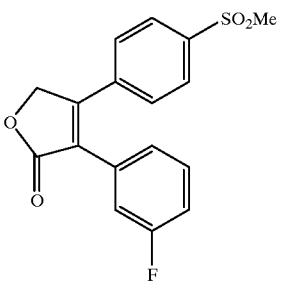 |
| 0.46 | 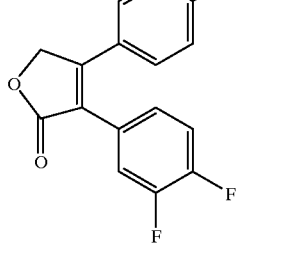 |
| 0.76 | 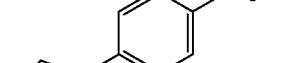 |
| 0.48 | 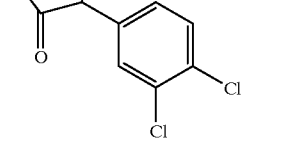 |
| 0.46 | 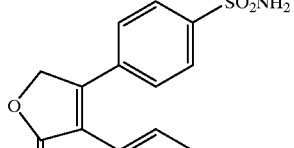 |
| 0.26 | 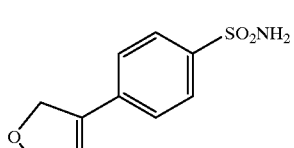 |

TABLE IV-continued

| ED30 (mg/kg) | STRUCTURE |
|---|---|
| 0.55 | (furanone with 4-SO₂Me-phenyl and 4-Br-3-F-phenyl substituents) |
| 0.25 | (5,5-dimethyl furanone with 4-SO₂Me-phenyl and 3-Cl-phenyl substituents) |
| 0.1–.3 | (5,5-dimethyl furanone with 4-SO₂Me-phenyl and 2-naphthyl substituents) |
| ~0.10 | (5,5-dimethyl furanone with 4-SO₂Me-phenyl and 3,4-difluorophenyl substituents) |
| 0.13 | (5,5-dimethyl furanone with 4-SO₂Me-phenyl and 3,4-dichlorophenyl substituents) |
| 0.07 | (5,5-dimethyl furanone with 4-SO₂Me-phenyl and 4-Cl-phenyl substituents) |

The invention will now be illustrated by the following non-limiting examples in which, unless stated otherwise:

(i) all operations were carried out at room or ambient temperature, that is, at a temperature in the range 18–25° C.; evaporation of solvent was carried out using a rotary evaporator under reduced pressure (600–4000 pascals: 4.5–30 mm. Hg) with a bath temperature of up to 60° C.; the course of reactions was followed by thin layer chromatography (TLC) and reaction times are given for illustration only; melting points are uncorrected and 'd' indicates decomposition; the melting points given are those obtained for the materials prepared as described; polymorphism may result in isolation of materials with different melting points in some preparations; the structure and purity of all final products were assured by at least one of the following techniques: TLC, mass spectrometry, nuclear magnetic resonance (NMR) spectrometry or microanalytical data; yields are given for illustration only; when given, NMR data is in the form of delta (d) values for major diagnostic protons, given in parts per million (ppm) relative to tetramethylsilane (TMS) as internal standard, determined at 300 MHz or 400 MHz using the indicated solvent; conventional abbreviations used for signal shape are: s. singlet; d. doublet; t. triplet; m. multiplet; br. broad; etc.: in addition "Ar" signifies an aromatic signal; chemical symbols have their usual meanings; the following abbreviations have also been used v (volume), w (weight), b.p. (boiling point), m.p. (melting point), L (liter(s)), mL (milliliters), g (gram (s)), mg (milligrams(s)), mol (moles), mmol (millimoles), eq (equivalent(s)).

The following abbreviations have the indicated meanings:

| | |
|---|---|
| Ac | acetyl |
| Bn = | benzyl |
| DBU = | 1,8-diazabicyclo [5.4.0]undec-7-ene |
| DIBAL = | diisobutylaluminum hydride |
| DMAP = | 4-(dimethylamino)pyridine |
| DMF = | N,N-dimethylformamide |
| Et₃N = | triethylamine |
| LDA = | lithium diisopropylamide |
| m-CPBA = | metachloroperbenzoic acid |
| MMPP = | monoperoxyphthalic acid |
| MPPM = | monoperoxyphthalic acid, magnesium salt 6H₂O |
| Ms = | methanesulfonyl = mesyl = SO₂Me |
| MsO = | methanesulfonate = mesylate |
| NSAJD = | non-steroidal anti-inflammatory drug |
| OXONE ® = | 2KHSO₅.KHSO₄.K₂SO₄ |
| PCC = | pyridinium chlorochromate |
| PDC = | pyridinium dichromate |

-continued

| | |
|---|---|
| Ph = | phenyl |
| Phe = | benzenediyl |
| Pye = | pyridinediyl |
| r.t. = | room temperature |
| rac. = | racemic |
| SAM = | aminosulfonyl or sulfonamide or $SO_2NH_2$ |
| TBAF = | tetra-n-butylammonium fluoride |
| Th = | 2- or 3-thienyl |
| TFAA = | trifluoroacetic acid anhydride |
| THF = | tetrahydrofuran |
| Thi = | thiophenediyl |
| TLC = | thin layer chromatography |
| TMS-CN = | trimethylsilyl cyanide |
| Tz = | 1H (or 2H)-tetrazol-5-yl |
| $C_3H_5$ = | allyl |

| Alkyl Group Abbreviations | |
|---|---|
| Me | methyl |
| Et = | ethyl |
| n-Pr = | normal propyl |
| i-Pr = | isopropyl |
| n-Bu = | normal butyl |
| i-Bu = | isobutyl |
| s-Bu = | secondary butyl |
| t-Bu = | tertiary butyl |
| c-Pr = | cyclopropyl |
| c-Bu = | cyclobutyl |
| c-Pen = | cyclopentyl |
| c-Hex = | cyclohexyl |

Example 1

3-(4-Aminosulfonyl)phenyl)-2-(4-fluorophenyl)-5-(2-hydroxy-2-propyl)thiophene

Step 1: 1-(4-Fluorophenyl)-2-(4-(methylthio)phenyl) ethanone

To 4-fluorobenzaldehyde (5.40 g) in 1,2-dichloroethane (43.50 mL) were added TMS-CN (4.32 g) and ZnI2 (44 mg). After 0.5 h at r.t., the solvent was removed in vacuo. To the resulting TMS cyanohydrin (9.20 g) in THF (42.0 mL) at −78° C. was added dropwise a solution of LDA 0.51M in THF (88.9 mL). After a period of 0.5 h, a THF solution (30.0 mL) of 4-(chloromethyl)thioanisole (9.93 g) was added dropwise over 0.5 h. After 18 h at +5° C., the resulting mixture was treated with TBAF (57.5 mL) followed by a 25% aqueous solution of $NH_4OAc$ (100 mL) and extracted with EtOAc (2 x 150 mL). After evaporation, a 10:1 mixture of Et2O and hexane (200 mL) was added to the crude ketone. After stirring for 10 h and filtration, the title product was obtained as a solid by filtration (2.40 g). $^1H$ NMR ($CD3COCD_3$): d 2.45 (3H, s), 4.34 (2H, s), 7.19–7.29 (6H, m), 8.14 (2H, q).

Step 2: Cis,trans-3-chloro-3-(4-fluorophenyl)-2-(4-(methylthio)-phenyl)propenal

To a solution of 1-(4-fluorophenyl)-2-(4-(methylthio) phenyl ethanone (2.50 g) in 1,2-dichloroethane (27.0 mL) were introduced the Vilsmeier reagent (Aldrich catalog, 1992–1993) 3.3M (11.6 mL) and DMAP (1.17 g). After a period of 4 h at 80° C., the reaction mixture was extracted with EtOAc and 25% aqueous solution of $NH_4OAc$. After evaporation in vacuo and drying for a few hours, the title product was used as such for the next step. 1H NMR ($CD_3COCD_3$): d 2.40 and 2.48 (3H, 2s), 6.90–7.80 (8H, m), 9.55 (1H, s).

Step 3: 5-(4-Fluorophenyl)-4-(4-(methylthio)phenyl) thiophene-2-carboxylic acid methyl ester To a solution of cis,trans 3-chloro-3-(4-fluorophenyl)-2-(4-(methylthio)phenyl)propenal (3.00 g) in pyridine (12.0 mL) were added methyl thioglycolate (1.16 mL) and Et3N (4.09 mL). The resulting mixture was then heated at 80° C. for 2 h. After extraction with EtOAc and washing with 3N HCl, the title product was purified by flash chromatography (30% EtOAc in hexane) (2.00 g). $^1H$ NMR ($CD_3COCD_3$): d 2.48 (3H, s), 3.88 (3H, s), 7.11 (2H, t), 7.21 (4H, s), 7.37 (2H, q), 7.80 (1H, s).

Step 4: 5-(4-Fluorophenyl)-4-(4-(methylsulfinyl)phenyl) thiophene-2-carboxylic acid methyl ester To a solution of 5-(4-fluorophenyl)-4-(4-(methylthio) phenyl)-thiophene-2-carboxylic acid methyl ester (5.60 g) in $CH_2Cl_2$ (84.0 mL) at 0° C. was added portionwise m-CPBA 50 to 60% (5.39 g). After TLC showed completion (50% EtOAc in hexane), the reaction mixture was extracted with saturated $NaHCO_3$, dried over $Na_2SO_4$, filtered and evaporated to dryness to provide the title compound as a white foam (5.00 g). $^1H$ NMR (CD3COCD$_3$): d 2.75 (3H, s), 3.92 (3H, s), 7.15 (2H, t), 7.40 (2H, q), 7.52 (2H, d), 7.66 (2H, d), 7.90 (1H, s).

Step 5: 4-(4-(Aminosulfonyl)phenyl)-5-(4-fluorophenyl) thiophene-2-carboxylic acid methyl ester 5-(4-Fluorophenyl)-4-(4-(methylsulfinyl)phenyl) thiophene-2-carboxlic acid methyl ester (0.500 g) was dissolved in TFAA (10.0 mL) and refluxed for 0.5 h. The solvent was then removed in vacuo and the resulting residue was co-evaporated 10 times-with a Et3N-MeOH solution (1:1) (100.0 mL) to provide a viscous oil after pumping for a few hours. The oil was dissolved in HOAc (10.0 mL) and treated at +10° C. with Cl2 in HOAc (1.9M) (3.5 mL). After 20 min., the solvent was removed under reduced pressure and after pumping, THF (20.0 mL) was added to the resulting mass of product. After bubbling $NH_3$ through for a few minutes at 0° C., the reaction mixture was stirred for 0.5 h at r.t. After extraction with EtOAc—25% NH4OAc solution and flash chromatography (30 to 40% EtOAc in hexane), the title product was obtained as a white solid (0.210 g). $^1H$ NMR ($CD_3COCD_3$): d 3,90 (3H, s), 6.55 (2H, bs), 7.13 (2H, t), 7.40 (2H, q), 7.46 (2H, d), 7.83 (2H, d), 7.90 (1H, s).

Step 6: 3-(4-Aminosulfonyl)phenyl)-2-(4-fluorophenyl)-5-(2-hydroxy-2-propyl)thiophene To 4-(4-aminosulfonyl)phenyl)-5-(4-fluorophenyl) thiophene-2-carboxylic acid methyl ester (0.460 g) in THF (5.70 mL) at 0° C. was added MeMgBr (1.4M) in toluene-THF solution (5.00 mL). The mixture was then stirred at r.t. for a few hours. The reaction was quenched by the addition of 25% $NH_4OAc$ solution, extracted with EtOAc and dried over with $Na_2SO_4$. The title compound was purified by flash chromatography (40 to 50% EtOAc in hexane) (0.300 g). 1H NMR ($CD_3COCD_3$): d 1.65 (6H, s), 4.52 (1H, s), 6.55 (2H, bs), 7.09 (3H, m), 7.34 (2H, dd), 7.30 (2H, m), 7.43 (2H, d), 7.82 (2H, d). Anal. calcd. for $C_{19}H_{18}FNO_3S_2$; C, 58.31; H, 4.60; N. 3.58. Found: C, 57.94; H, 4.66; N, 3.44

Example 2

3-(4-(Aminosulfonyl)phenyl)-2-(4-fluorophenyl)thiophene

Step 1: 4-(4-(Aminosulfonyl)phenyl)-5-(4-fluorophenyl) thiophene-2-carboxylic acid To a solution of 4-(4-(aminosulfonyl)phenyl)-5-(4-fluorophenyl)thiophene-2-carboxylic acid methyl ester (Example 1, Step 5) (0.210 g) in THF (2.0 mL) were added MeOH (1.0 mL), NaOH lN (1.0 mL) and a few drops of NaOH lON. The resulting mixture was heated at 45° C. for 2 h and the reaction was then partitioned between EtOAc and HCl (3N) to provide the title product as a white solid (0.200 g). $^1H$ NMR ($CD_3COCD_3$) d 6.60 (2H, s), 7.15 (2H, t), 7.35 (2H, q), 7.45 (2H, d), 7.82 (2H, d), 7.87 (1H, s).

Step 2: 3-(4-(Aminosulfonyl)phenyl)-2-(4-fluorophenyl) thiophene

To a solution of 3-(4-(aminosulfonyl)phenyl)-2-(4-fluorophenyl)thiphene-2-carboxylic acid (0.280 g) in quinoline (4.0 mL) was added Cu bronze (0.300 g). After 0.5 h at 180° C. under nitrogen, the reaction mixture was extracted with EtOAc and HCl 3N, dried over $Na_2SO_4$ and purified by flash chromatography (30% EtOAc in hexane) to give the title compound as a white solid (0.180 g). $^1$H NMR ($CD_3COCD_3$): d 6.60 (2H, bs), 7.15 (2H, t), 7.29 (1H, d), 7.35 (2H, q), 7.45 (2H, d), 7.60 (1H, d), 7.83 (2H, d).

Anal. calcd for $C_{16}H_{12}FNO_2S_2$; C, 57.65; H, 3.60; N, 4.20. Found: C, 57.62; H, 3.59; N, 4.15.

Example 3
3-(4-(Aminosulfonyl)phenyl)-2-(4-fluorophenyl)-5-(2-propyl)thiophene $^1$H NMR ($CD_3COCD_3$) d 1.40 (6H, d), 3.25 (1H, septuplet), 6.58 (2H, bs), 7.05 (1H, s), 7.15 (2H, t), 7.32 (2H, dd), 7.46 (2H, d), 7.80 (2H, d).

Anal. calcd. for $Cl_9H_{18}FNO_2S_2$. C, 60.80; H, 4.80; N, 3.73. Found: C, 60.59; H, 4.45; N, 3.60.

Example 4
3-(4-(Aminosulfonyl)phenyl)-2-cyclohexylthiophene $^1$H NMR $(CD_3)_2)CO$) d 1.24–1.40 (3H, m), 1.40–1.56 (2H, m), 1.65–1.85 (3H, m), 1.90–2.0 (2H, m), 3.18 (1H, m), 6.58 (2H, bs), 7.05 (1H, d), 7.37 (1H, d), 7.58 (2H, d), 7.97 (2H, d).

Example 5
5-(4-Carboxyphenyl)-4-(4-(methylsulfonyl)phenyl) thiophene-2-carboxylic acid
Step 1: 4-(2-(4-Methylthiophenyl)-l-oxo-ethyl)benzoic acid methyl ester To methyl 4-formylbenzoate (10.30 g) in 1,2-dichloroethane at r.t. were added TMS-CN (6.58 mL) and $ZnI_2$ (2.00 g), after 0.5 h at r.t., the solvent was removed in vacuo. To the resulting TMS cyanohyrin (5.00 g) in THF (22.0 mL) at −78° C. was added dropwise a solution of LDA 0.87 M in THF (26.2 mL). After a period of 0.5 h, a THF solution (10.0 mL) of 4-(chloromethyl)thioanisole was added dropwise over 0.5 h. The temperature was then brought slowly to −20° C. then to 5° C. for 2 h and TBAF IM in THF (50.0 mL) was added. After the addition of 25% aqueous solution of $NH_4OAc$, the reaction mixture was extracted with EtOAc, dried over $NASO_4$, evaporated in vacuo and purified by flash chromatography (20 to 30% EtOAc in hexane) to afford the title compound as a white solid (7.00 g).

Step 2: 4-(1-Oxo-2-(4-(methylsulfonyl)phenyl)ethyl) benzoic acid methyl ester

To 7.10 g of 4-(2-(4-methylthiophenyl)-1-oxo-ethyl) benzoic acid methyl ester in MeOH (100 mL) was added oxone (21.0 g) in $H20$ (20.0 mL) at 0° C. After a few hours at r.t., the reaction mixture was extracted with EtOAc and $H_2O$ to afford after flash chromatography (50 to 100% EtOAc in hexane), the title product as a white solid (3.20 g). $^1$H NMR (CD3COCD3) d 3.10 (3H, s), 3.95 (3H, s), 4.65 (2H, s), 7.60 (2H, d), 7.96 (2H, d), 8.20 (4H, q).

Step 3: Cis,trans 4-(1-Chloro-3-oxo-2-(4-(methylsulfonyl) phenyl)-1-propenyl)benzoic acid methyl ester To a solution of 4-(1-oxo-2-((4-methylsulfonyl)phenyl) ethyl) benzoic acid (1.70 g) in 1,2-dichloroethane (.15.0 mL) were added the Vilsmeier reagent 3.3 M (6.2 mL) and DMAP (0.624 g). The resulting mixture was heated at 80° C. for 4 h. The reaction mixture was then extracted with 25% aqueous solution of $NH_4OAc$ and EtOAc. After drying over $Na_2SO_4$ and evaporation the title compound was obtained as an oil and used as such for the next step.

Step 4: 5-(4-(Methoxycarbonyl)phenyl)-4-(4-(methylsulfonyl)-phenyl)thiophene-2-carboxylic acid methyl ester Prepared from 4-(1-chloro-3-oxo-2-(4-methylsulfonyl)-phenyl)-1-propenyl)benzoic acid methyl ester as for Example 1, Step 3. $^1$H NMR ($CD_3COCD_3$) d 3.13 (3H, s), 3.85 and 3.92 (6H, 2s), 7.50 (2H, d), 7.55 (2H, d), 7.90 (2H, d), 7.92 (1H, s), 7.92 (2H, d).

Step 5: 5-(4-(Carboxyphenyl)-4-(4-(methyl)sulfonyl) phenyl)-thiophene-2-carboxylic acid Prepared from 5-(4-(methoxycarbonyl)phenyl)-4-(4-(methyl)sulfonyl)phenyl) thiophene-2-carboxylic acid methyl ester as for Example 2, Step 1.

$^1$H NMR ($CD_3COCD_3$) d 3.15 (3H; s), 7.50 (2H, d), 7.62 (2H, d), 7.95 (2H, d), 7.98 (1H, s), 8.05 (2H, d).

Anal calcd. for $C_{19}H_{14}O_6S_2 \cdot 0.1 H_2O$: C, 56.46; H, 3.51. Found: C, 56.18; H, 3.51.

Example 6
4-(4-Fluorophenyl)-2-methyl-5-(4-(methylsulfonyl)phenyl) thiazole
Step 1: 1-(4-Fluorophenyl)-2-(4-(methylsulfonyl)phenyl) ethanone To 1-(4-Fluorophenyl)-2-(4-(methylthio)phenyl)ethanone of Example 1, Step 1 (17.9 g) in a solution of $CH_2Cl_2$-MeOH (272.0 mL/27.0 mL) at 0° C. was added MPPM (28.0 g). The cooling bath was then removed and the reaction mixture stirred at r.t. for 1 h. At 0° C., additional MPPM (28.0 g) was added and the reaction mixture kept for 1.5 h at r.t. The insoluble material was filtered followed by evaporation of the solvents, the residue was then extracted with $CH_2Cl_2$—$NaHCO_3$. After evaporation in vacuo, the resulting solid was washed with ether-hexane (1:1) and filtered to provide the title compound 16.8 g.

$^1$H NMR ($CD_3COCD_3$) d 3.13 (3H, s), 3.58 (2H, s), 7.29 (2H, t), 7.55 (2H, d), 7.88 (2H, d), 8.20 (2H, dd).

Step 2: 2-Bromo-1-(44-fluorophenyl)-2-(4-(methylsulfonyl) phenyl)-ethanone

To 1-(4-Fluorophenyl)-2-(4-(methylsulfonyl)phenyl) ethanone (1.00 g) in $CH_2Cl_2$ containing $CHCl_3$ (1.0 mL) and $CCl_4$ (1.0 mL) was added bromine (0.614 g). After shining light for 1 h, the reaction was quenched with $Na_2SO_4$, extracted with $CH_2Cl_2$, dried over $Na_2SO_4$ and evaporated to yield the title compound which was used as such for the next step (1.10 g). $^1$H NMR ($CD_3COCD_3$) d 3.10 (3H, s), 7.05 (1H, s), 7.30 (2H, t), 7.87 (2H, d), 7.95 (2H, d), 8.25 (2H, .dd).

Step 3: 4-(4-Fluorophenyl)-2-methyl-5-(4-(methylsulfonyl) phenyl)-thiazole

To 2-bromo-1-(4-fluorophenyl)-2-(4-(mthylsulfonyl) phenyl)-ethanone (1.10 g) in ethanol (15.0 mL) were added thioacetamide (0.266 g) and pyridine (0.300 mL). After refluxing for 2 h, the reaction mixture was extracted with EtOAc, 25% $NH_4OAc$ and purified by flash chromatography (50% EtOAc in hexane then 90% $Et_2O$ in hexane) to yield the title compound (0.320 g). $^1$H NMR ($CD_3COCD_3$) d 2.72 (3H, s), 3.15 (3H, s), 7.09 (2H, t), 7.52 (2H, dd), 7.60 (2H, d), 7.92 (2H, d). Anal. calcd. for $C_{17}H_{14}FNO_2S_2$: C, 58,78; H, 4.03; N, 4.03. Found: C, 58.71, H, 4.17; N, 3.85.

Example 7
2-(4-Fluorophenyl)-3-(4-(methylsulfonyl)phenyl)-2-cyclopenten-1-one
Step 1: 1-(4-Fluorophenyl)-5-hexen-2-one To a suspension of 14.6 g (80 mmol) of $CdCl_2$ in 200 niL of ether cooled to 0° C. was added 115 mL of 1.3 M solution of 3-butene-1-magnesium bromide dropwise. The mixture was refluxed for 1 h and ether was then removed by distillation. Benzene (500 mL) was introduced, followed by a solution of 17.5 g (100 mmol) 4-fluorophenylacetyl chloride. After refluxing for 1 h, the reaction mixture was quenched with 200 mL of saturated aqueous $NH_4Cl$, 50 mL of 1 N HCl, and extracted with 200 mL of 1:1 hexane/EtOAC. The organic phase was dried over $MgSO_4$ and concentrated. The residue was purified by flash chromatography eluted with 4:1 hexane/EtOAc to give 15 g of the title product. $^1H$ NMR ($CDCl_3$) d 2.40 (2H, t), 2.53 (2H, t), 3.63 (2H, s), 4.90–4.98 (2H, m), 5.67–5.78 (1H, m), 6.98 (2H, t), 7.13 (2H, m).

Step 2: 1-(4-Fluorophenyl)-5-oxo-2-pentanone

A solution of 14 g of 1-(4-fluorophenyl)-5-hexen-2-one in 200 mL of 3:1 $CH_2Cl_2$/MeOH was cooled to −78° C. and treated with excess ozone. The resulting mixture was treated with 15 g of triphenylphosphine and stirred at room temperature for 1 h. The reaction mixture was concentrated and flash chromatographed with 3:1 hexane/EtOAc to give 8 g of the title ketoaldehyde.

$^1H$ NMR ($CDCl_3$) d 2.72 (4H, s), 3.71 (2H, s), 6.99 (2H, t), 7.14 (2H, m), 9.73 (1H, s).

Step 3: 2-(4-Fluorophenyl)-2-cyclopenten-1-one

A solution of 8 g of 1-(4-fluorophenyl)-5-oxo-2-pentanone in 300 mL of MeOH was treated with 2 g of NaOMe. The mixture was stirred for 2 h and then quenched with 5 mL of HOAc. The solvent was evaporated and the residue purified by flash chromatography, eluting with 3:1 hexane/EtOAc to give 7 g of the title product. 1H NMR ($CDCl_3$) d 2.57 (2H, m), 2.68 (2H, m), 7.04 (2H, J=8.8 Hz, t), 7.67 (2H, J=8.8, 5.5 Hz, dd), 7.77 (1H, m).

Step 4: 1-(4-(Methylthio)phenyl)-2-(4-fluorophenyl)-2-cyclopenten-1-ol

To a solution of 3.86 g (19 mmol) of 4-bromothioanisole in 90 mL of Et2O cooled at −78° C., was added 22 mL of 1.7 M solution of t-BuLi in pentane (38 mmol) dropwise. The reaction mixture was stirred for 15 min at −78° C. and a solution of 2.23 g of 2-(4-Fluorophenyl)-2-cyclopenten-1-one in 10 mL of $Et_2O$ was added. After stirring for 15 min at −78° C., the reaction mixture was warmed to 0° C., and quenched with 50 mL of sat. $NH_4Cl$. The product was extracted with 100 mL EtOAc, dried over $Na_2SO_4$, and purified by flash chromatography, eluted with 4:1 hexane/EtOAc to give 3.4 g of the desired product. 1H NMR ($CDCl_3$) d 2.12 (1H, s), 2.34 (2H, m), 2.44 (3H, s), 2.45–2.52 (1H, m), 2.56–2.65 (1H, m), 6.37 (1H, m), 6.84 (2H, J=8.7 Hz, t), 7.17 (2H, J=8.3 Hz, d), 7.24–7.33 (4H, m).

Step 5: 2-(4-Fluorophenyl)-3-(4-(methylthio)phenyl)-2-cyclo-penten-1-one

To a suspension of PCC (4.5 g, 20.9 mmol) and 10 g of anhydrous 4 Å molecular sieves in 150 mL of $CH_2Cl_2$ was added a solution of 2.2 g (7.3 mmol) of 1-(4-(methylthio)phenyl)-2-(4-fluorophenyl)-2-cyclopenten-1-ol in 20 mL $CH_2Cl_2$. The mixture was stirred for 1 h at r.t. and then diluted with 300 mL of $Et_2O$. After filtration and concentration, the residue was flash chromatographed with 2:1 hexane/EtOAc to give 1.5 g of the title product. 1H NMR ($CDCl_3$) d 2.45 (3H, s), 2.68 (2H, m), 3.00 (2H, m), 7.02 (2H, J=8.6 Hz, t), 7.11 (2H, J=8.6 Hz, d), 7.15–7.23 (4H, m).

Step 6: 2-(4-Fluorophenyl)-3-(4-(methylsulfonyl)phenyl)-2-cyclopenten-1-one

To a solution of 50 mg (0.17 mmol) of 2-(4-Fluorophenyl)-3-(4-methylthio)phenyl)-2-cyclopenten-1-one in 8 mL of 10:1 $CH_2Cl_2$/MeOH was added 124 mg (0.2 mmol) of MPPM. The reaction mixture was stirred at room temperature for 2 h and then diluted with 10 mL of 1:1 hexane/EtOAc. After filtration and concentration, the residue was purified by flash chromatography eluted with 2:1 EtOAc/hexane to give 45 mg of the title product. $^1H$ NMR (acetone-d6) d 2.67 (2H, m), 3.14 (3H, s), 3.16 (2H, m), 7.05–7.10 (2H, m), 7.20–7.25 (2H, m), 7.63 (2H, d), 7.93 (2H, d).

Example 8

4-(4-(Methylsulfonyl)phenyl)-5-(4-fluorophenyl)-isothiazole

To a solution of 338 mg (1 mmol) of cis,trans 3-chloro-3-(4-fluorophenyl)-2-(4-(methylsulfonyl)phenyl)propenal in 5 mL of acetone was added 230 mg (3 mmol) of $NH_4SCN$. The reaction mixture was refluxed for 3 h, and then quenched with 20 mL of saturated $NaHCO_3$. The product was extracted with 100 mL of EtOAc, dried over $Na_2SO_4$, concentrated and purified by flash chromatography eluted with 3:2 hexane/EtOAc to give 250 mg of the title product. 1H NMR ($CDCl_3$) d 8.57 (1H, s), 7.93 (3H, d), 7.50 (2H, d), 7.30 (2H, t), 7.08 (2H, t).

Example 9

3-(4-Fluorophenyl)-4-(4-(methylsulfonyl)phenyl)-2-(5H)-furanone

Step 1: 2-Bromo-1-(4-(methylsulfonyl)phenyl)ethanone

A solution of 197 g of 4-(Methylthio)acetophenone (ref: JACS, 1952, 74, p. 5475) in 700 mL of MeOH and 3500mL of $CH_2Cl_2$ was added 881 g of MMPP over a period of 30 min. After 3 h at room temperature the reaction mixture was filtered and the filtrate was washed with 2 L of saturated aqueous solution of $NaHCO_3$ and 1 L of brine. The aqueous phase was further extracted with 2 L of $CH_2Cl_2$. The combined extracts was dried over $Na_2SO_4$ concentrated to give 240 g of 4-(methylsulfonyl)acetophenone as a white solid.

To a cooled (−5° C.) solution of 174 g of 4-(methylsulfonyl)acetophenone in 2.5 L of $CHCl_3$ was added 20 mg of $AlCl_3$, followed by a solution of 40 mL of $Br_2$ in 300 mL $CHCl_3$. The reaction mixture was then treated with 1.5 L of water and the $CHCl_3$ was separated. The aqueous layer was extracted with 1 L of EtOAc. The combined extracts was dried over Na2SO4 and concentrated. The crude product was recystalized from 50/50 EtOAc/hexane to give 210 g of 2-bromo-1-(4-(methylsulfonyl)phenyl)ethanone as a white solid.

Step 2:

To the product of Step 1 (216 mg) dissolved in acetonitrile (4 mL) was added Et3N (0.26 mL), followed by 4-fluorophenylacetic acid (102 mg). After 1.5 h at room temperature 0.23 nL of DBU was added. The reaction mixture was stirred for another 45 min and then treated with 5 mL of IN HCl. The product was extracted with EtOAc, dried over Na2S04 and concentrated. The residue was purified by flash chromatography (40% EtOAc in hexane) to yield 150 mg of the title compound as a solid. $^1H$ NMR ($CD_3COCD_3$) d 3.15 (3H, s), 5.36 (3H, s), 7.18 (2H, J=8.9 Hz, t), 7.46 (2H, m), 7.7 (2H, J=8.65 Hz, d), 7.97 (2H, J=8.68, d).

Example 10

3-(4-Fluorophenyl)-4-(4-(aminosulfonyl)phenyl)-2-(2H)-furanone 1H NMR ($CD_3COCD_3$) d 5.34 (2H, s), 6.67 (2H, bd), 7.18 (2H, m), 7.46 (2H, m), 7.61 (2H, m), 7.90 (2H, m). M.P. 187–188° C. (d).

Example 11

3-(4-Fluorophenyl)-4-(4-(methylsulfonyl)phenylfuran

Step 1:

Using the product of Example 10, (0.2 g) in THF (5 mL) and toluene (3 mL) was added slowly at −78° C. a solution of DIBAL (0.72 mL, 1M in toluene). After 15 min, the solution was warmed up to 0° C. for another 15 min. This mixture was then poured into a chilled aqueous solution of sodium potassium tartrate and EtOAc. The organic layer was stirred for 0.5 h with a few crystals of camphor sulfonic acid. This solution was then concentrated and purified by flash chromatography to yield the title compound. $^1$H NMR (CDCl$_3$) 3.1 (3H, s), 7.02 (2H, J=8.9, t), 7.18 (2H, m), 7.4 (2H, J=8.8 Hz, d), 7.58 (1H, s), 7.68 (1H, s), 7.85 (2H, J=8.8 Hz, d)

Example 12

5,5-Dimethyl-3-(4-fluorophenyl)-4-(4-methylsulfonylphenyl)-2-(5H)-furanone

Step 1: Methyl 2-trimethylsilyloxyisobutyrate

To a solution of 1.2 mL (10.4 mmol) of methyl 2-hydroxy-isobutyrate in 50 mL of CH$_2$Cl$_2$ were added 1.2 g (17.6 mmol) of imidazole and 2.1 mL (16.6 mmol) of TMSCl. The mixture was stirred at r.t. for 1.5 h and quenched with 20 mL of H$_2$O. The organic layer was dried over MgSO$_4$, concentrated and passed through a short plug of silica gel eluted with 9:1 hexane/EtOAc. Evaporation of solvent afforded 1.27 g of the title compound as a colorless oil. $^1$H NMR (CD$_3$COCD$_3$) d 0.08 (9H, s), 1.38 (6H, s), 3.67 (3H, s).

Step 2: 2-Trimethylsilyloxy-4'-(methylthio)isobutyrophenone

A solution of 204 mg (1.0 mmol) of 4-bromothioanisole in 2.5 mL of THF was cooled to −78° C. and treated with 0.42 mL of 2.5 M n-BuLi solution in hexane. After stirring at −78° C. for 1 h, a solution of 380 mg (2.0 mmol) of methyl 2-trimethylsilyloxyisobutyrate in 2 mL of THF was added. The mixture was stirred at −78° C. for 2 h and then quenched with NH$_4$OAc buffer. The product was extracted with EtOAc, dried over MgSO$_4$ and concentrated. The residue was purified by flash chromatography, eluting with 19:1 hexane/EtOAc to give 95 mg of the title product. $^1$H NMR (CD$_3$COCD$_3$) d 0.05 (9H, s), 1.52 (6H, s), 2.53 (3H, s), 7.33 (2H, d), 8.12 (2H, d).

Step 3: 2-Hydroxy-4'-(methylthio)isobutyrophenone

To a solution of 40 mg (0.14 mmol) of 2-trimethylsilyloxy-4'-(methylthio)isobutyrophenone in 2 niL TEF was added 0.2 mL of 1 M n-Bu$_4$NF in THF. The resulting mixture was stirred for 30 min and then quenched with 10 mL of NH4OAc buffer. The product was extracted with EtOAc, dried over MgSO4 and concentrated. The residue was purified by flash chromatography, eluting with 4:1 hexane/EtOAc to give 25 mg of the tide product. $^1$H NMR (CD$_3$COCD$_3$) d 1.50 (6H, s), 2.54 (3H, s), 4.68 (1H, s), 7.30 (2H, d), 8.15 (2H, d).

Step 4: 2-(4-Fluorophenylacetoxy)-4'-(methylthio)isobutyrophenone To a solution of 72 mg (0.34 mmol) 2-hydroxy-4'-(methylthio)isobutyrophenone in 1.7 mL of CH$_2$Cl$_2$ were added 0.2 mL of pyridine and 140 mg (0.81 mmol) of 4-fluorophenylacetyl chloride. The mixture was stirred at room temperature overnight and then quenched with NH$_4$OAc buffer. The product was extracted with EtOAc, dried over MgSO$_4$ and concentrated. The crude product was purified by flash chromatography eluting with 8:1 hexane/EtOAc to give 95 mg of the title product. $^1$H NMR (CD$_3$COCD$_3$) d 1.62 (3H, s), 1.67 (3H, s), 2.48 (3H, s), 3.79 (2H, s), 7.0–7.3 (6H, m), 7.78 (2H, d).

Step 5: 5,5-Dimethyl-3-(4-fluorophenyl-4-(4-methylthiophenyl)-2-(5H)-furanone

To a solution of 95 mg of 2-(4-fluorophenylacetoxy)-4'-(methylthio)-isobutyrophenone in 4 mL of CH$_2$Cl$_2$ was added 0.2 mL of 1,8-diazabicyclo(5.4.0)undec-7-ene. The mixture was stirred for 4 h and diluted with NH$_4$OAc buffer. The product was extracted with EtOAc, dried over MgSO$_4$ and concentrated. The residue was purified by flash chromatography, eluting with 20:1 toluene/EtOAc to give 75 mg of the title product. 1H NMR (CD$_3$COCD$_3$) d 1.58 (6H, s), 2.50 (3H, s), 7.03 (2H, dd), 7.25–7.35 (4H, m), 7.41 (2H, dd).

Step 6: 5,5-Dimethyl-3-(4-fluorophenyl)-4-(4-methylsulfonylphenyl)-2-(5H)-furanone To a solution of 81 mg of 5,5-dimethyl-3-(4-fluorophenyl)-4-(4-methyl-thiophenyl)-2-oxo-2H-dihydrofuran in 1.8 mL of CH$_2$Cl$_2$ and 0.2 mL of MeOH was added 250 mg of MPPM. The reaction mixture was stirred at room temperature for 1 h and then quenched with aqueous NaHCO$_3$. The product was extracted with EtOAc, dried over MgSO$_4$ and concentrated. The crude product was purified by flash chromatography eluting with 1:1 hexane/EtOAc to give 73 mg of the title product. $^1$H NMR (CD$_3$COCD$_3$) d 1.62 (6H, s), 3.15 (3H, s), 7.02 (2H, dd), 7.40 (2H, dd), 7.65 (2H, d), 8.03 (2H, d).

Example 13

2-((4-aminosulfonyl)phenyl)-3-(4-fluorophenyl)thiophene $^1$H NMR (CD$_3$COCD$_3$) d 6.60 (2H, bs), 7.12 (2H, t), 7.25 (1H, d), 7.35 (2H, m), 7.45 (2H, d), 7.65 (1H, d), 7.85 (2H, d).

Analysis calculated for C$_{16}$H$_{12}$FNS$_2$O$_2$ C, 57.65; H, 3.60; N, 4.20 Found: C, 57.55; H, 3.79; N, 4.03

Example 14

3-(4-(Trifluoroacetylamninosulfonyl)phenyl)-2-(4-fluorophenyl)thiophene $^1$H NMR (300 MHz, CD3COCD3) d 7.15 (2H, t), 7.30 (3H, m), 7.45 (2H, d), 7.65 (1H, d), 7.95 (2H, d).

Example 15

3-(2,4-Difluorophenyl)-4-(4-(methylsulfonyl)phenyl)-2-(5H)-furanone

Analysis calculated for C$_{17}$H$_{12}$F$_2$O$_4$S C, 58.28; H, 3.45; S, 9.15 Found: C, 58.27; H, 3.50; S, 9.27

Example 16

3-(3.4-Difluorophenyl)-4-(4-(methylsulfonyl)phenyl)-2-(5H)-furanone

To a solution of 3,4-difluorophenylacetic acid (ALDRICH CHIMICAL) (10 g) and 2-bromo-1-(4-(methylsulfonyl)phenyl)ethanone (Example 9, Step 1) (17.3 g) in acetonitrile (200 mL) at room temperature was added slowly triethylamine (20.2 mL). After 1 h at room temperature, the mixture was cooled in an ice bath and treated with 17.4 mL of DBU. After 2 h at 0° C., the mixture was treated with 200 mL of 1N HCl and the product was extracted with EtOAc, dried over Na$_2$SO$_4$ and concentrated. The residue was applied on top of a silica gel plug (sintered glass funnel) eluted with 75% EtOAc/hexane, giving after evaporation of the solvent and swish in ethyl acetate, 10 g of the title compound.

Analysis calculated for C$_{17}$H$_{12}$F$_2$O$_4$S C, 58.28; H, 3.45; S, 9.15 Found: C, 58.02; H, 3.51; S, 9.35

Example 17

3-(2,6-Difluorophenyl)-4-(4-(methylsulfonyl)phenyl)-2-(5H)-furanone

Analysis calculated for C$_{17}$H$_{12}$F$_2$O$_4$S C, 58.28; H, 3.45; S, 9.15 Found: C, 58.18; H, 3.50; S, 9.44

Example 18

3-(2,5-Difluorophenyl)-4-(4-(methylsulfonyl)phenyl)-2-(5H)-furanone

Analysis calculated for $C_{17}H_{12}F_2O_4S$ C, 58.28; H, 3.45; S, 9.15 Found: C, 58.89; H, 3.51; S, 9.11

Example 19
3-(3,5-Difluorophenyl)-4-(4-(methylsulfonyl)phenyl)-2-(5H)-furanone Analysis calculated for $C_{17}H_{12}F_2O_4S$ C, 58.28; H, 3.45; S, 9.15 Found: C, 58.27; H, 3.62; S, 9.32

Example 20
3-(4-Bromophenyl)-4-(4-(methylsulfonyl)phenyl)-2-(5H)-furanone

Analysis calculated for $C_{17}H_{13}BrO_4S$ C, 51.94; H, 3.33; S, 8.16 Found: C, 51.76; H, 3.42; S, 8.21

Example 21
3-(4-Chlorophenyl)-4-(4-(methylsulfonyl)phenyl)-2-(5H)-furanone $^1$H NMR (300 MHz, $CDCl_3$) d 7.93 (2H, d), 7.49 (2H, d), 7.35 (4H, m), 5.16 (2H, s), 3.06 (3H, s)

Example 22
3-(4-Methoxyphenyl)-4-(4-(methylsulfonyl)phenyl)-2-(5H)-furanone

Analysis calculated for $C_{18}H_{16}O_5S$ C, 62.78 H, 4.68; S, 9.31 Found: C, 62.75; H, 4.72; S, 9.39

Example 23
3-(Phenyl)-4-(4-(methylsulfonyl)phenyl)-2-(5H)-furanone

To a solution of phenylacetic acid (27.4 g, 201 mmol) and 2-bromo-1-(4-(methylsulfonyl)phenyl)ethanone (Example 9, Step 1) (60 g, 216 mmol, 1.075 eq.) in acetonitrile (630 mL) at 25° C. was added slowly triethylamine (30.8 mL, 1.1 eq.). The mixture was stirred for 20 min. at room temperature and then cooled in an ice bath. DBU (60.1 mL, 3 eq.) was slowly added. After stirring for 20 min. in the ice bath, the reaction was complete and the mixture was acidified with 1N HCl (color changes from dark brown to yellow). Then 2.4 L of ice and water were added, stirred for a few minutes, then the precipitate was filtered and rinsed with water (giving 64 g of crude wet product). The solid was dissolved in 750 mL of dichloromethane (dried over $MgSO_4$, filtered) and 300 g of silica gel was added. The solvent was evaporated to near dryness (silica gel a bit sticky) and the residue was applied on top of a silica gel plug (sintered glass funnel) eluted with 10% EtOAc/$CH_2Cl_2$, giving after evaporation of the solvent and swish in ethyl acetate, 36.6 g (58%) of the title compound.

Analysis calculated for $C_{17}H_{14}O_4S$ C, 64.95; H, 4.49; S, 10.20 Found: C, 64.63; H, 4.65; S, 10.44

Example 24
3-(2-Chlorophenyl)-4-(4-(methylsulfonyl)phenyl)-2-(5H)-furanone

Analysis calculated for $C_{17}H_{13}ClO_4S$ C, 58.54; H, 3.76; S, 9.19 Found: C, 58.59; H, 3.80; S, 9.37

Example 25
3-(2-Bromo-4-fluorophenyl)-4-(4-(methylsulfonyl)phenyl)-2-(5H)-furanone Analysis calculated for $C_{17}H_{12}BrFO_4S$ C, 49.75; H, 2.93 Found: C, 49.75; H, 3.01

Example 26
3-(2-Bromo-4-Chlorophenyl)-4-(4-methylsulfonyl)phenyl)-2-(5H)-furanone $^1$H NMR (300 MHz, acetone-$d_6$) d 7.95 (2H, d), 7.85 (1H, d), 7.63 (2H, dd), 7.55 (1H, dd), 7.45 (1H, d), 5.50 (2H, s), 3.15 (3H, s)

Example 27
3-(4-Chloro-2-fluorophenyl)-4-(4-(methylsulfonyl)phenyl)-2-(5H)-furanone $^1$H NMR (300 MHz, acetone-d6) d 8.0 (2H, d), 7.70 (2H, d), 7.50–7.30 (3H, m), 5.35 (2h, s), 3.15 (3H, s)

Example 28
3-(3-Bromo-4-fluorophenyl)-4-(4-(methylsulfonyl)phenyl)-2-(5H)-furanone Analysis calculated for $C_{17}H_{12}BrFO_4S$ C, 49.75; H, 2.93 Found: C, 49.44; H, 2.98

Example 29
3-(3-Chlorophenyl)-4-(4-(methylsulfonyl)phenyl)-2-(5H)-furanone

Analysis calculated for $C_{17}H_{13}ClO_4S$ C, 58.54; H, 3.76 Found: C, 58.29; H, 3.76

Example 30
3-(2-Chloro-4-fluorophenyl)-4-(4-(methylsulfonyl)phenyl)-2-(5H)-furanone Analysis calculated for $C_{17}H_{12}ClFO_4S$ C, 55.67; H, 3.30 Found: C, 55.67; H, 3.26

Example 31
3-(2,4-Dichlorophenyl)-4-(4-(methylsulfonyl)phenyl)-2-(5H)-furanone Analysis calculated for $C_{17}H_{12}Cl_2O_4S$ C, 53.28; H, 3.16; S, 8.37 Found: C, 52.89; H, 3.23; S, 8.58

Example 32
3-(3 4-Dichlorophenyl)-4-(4-(methylsulfonyl)phenyl)-2-(5H)-furanone Analysis calculated for $C_{17}H_{12}Cl_2O_4S$ C, 53.28; H, 3.16; S, 8.37 Found: C, 53.07; H, 3.32; S, 8.51

Example 33
3-(2,6-Dichlorophenyl)-4-(4-(methylsulfonyl)phenyl)-2-(5H)-furanone Analysis calculated for $C_{17}H_{12}Cl_2O_4S$ C, 53.28; H, 3.16; S, 8.37 Found: C, 52.99; H, 3.22; S, 8.54

Example 34
3-(3-Chloro-4-fluorophenyl)-4-(4-(methylsulfonyl)phenyl)-2-(5H)-furanone $^1$H NMR (300 MHz, acetone-$d_6$) d 8.0 (2H, d), 7.70 (2H, d), 7.60 (1H, d), 7.25–7.40 (2H, m), 5.35 (2H, s), 3.15 (3H, s)

Example 35
3-(4-Trifluoromethylphenyl)-4-(4-(methylsulfonyl)phenyl)-2-(5H)-furanone $^1$H NMR ($CD_3COCD_3$) d 8.10 (2H, d), 7.82–7.93 (4H, m), 7.75 (2H, d), 5.55 (2H, s), 3.30 (3H, s)

Example 36
3-(3-Fluoro-4-methoxyphenyl)-4-(4-(methylsulfonyl)phenyl)-2-(5H)-furanone Analysis calculated for $C_{18}H_{15}OF_5S$ C, 59.66; H, 4.17 Found: C, 59.92; H, 4.37

Example 37
3-(3-Chloro-4-methoxyphenyl)-4-(4-(methylsulfonyl)phenyl)-2-(5H)-furanone Analysis calculated for $C_{18}H_{15}ClO_5S$ C, 57.07; H, 3.99 Found: C, 57.29; H, 4.15

Example 38
3-(3-Bromo-4-methoxyphenyl)-4-(4-(methylsulfonyl)phenyl)-2-(5H)-furanone Analysis calculated for $C_{18}H_{15}BrO_5S$ C, 51.08; H, 3.57 Found: C, 51.38; H, 3.62

Example 39
3-(2-Fluorophenyl)-4-(4-(methylsulfonyl)phenyl)-2-(5H)-furanone

Analysis calculated for $C_{17}H_{13}FO_4S$ C, 61.44; H, 3.94 Found: C, 61.13; H, 3.85

Example 40
3-(4-Methylthiophenyl)-4-(4-(methylsulfonyl)phenyl)-2-(5H)-furanone $^1$H NMR (300 MHz, acetone-$d_6$) d 8.0 (2H, d), 7.70 (2H, d), 7.35 (2H, d), 7.25 (2H, d), 5.35 (2H, s), 3.15 (3H, s), 2.55 (3H, s)

Example 41
3-(3-Fluorophenyl)-4-(4-(methylsulfonyl)phenyl)-2-(5H)-furanone $^1$H NMR (300 MHz, $CDCl_3$) d 7.93 (2H, d), 7.49 (2H, d), 7.35 (1H, m), 7.12 (3H, m), 5.18 (2H, s), 3.06 (3H, s)

Example 42
3-(2-Chloro-6-fluorophenyl)-4-4-(methylsulfonyl)phenyl)-2-(5H)-furanone $^1$H NMR (300 MHz, acetone-d6), d 8.0 (2H, d), 7.70 (2H, d), 7.55–7.65 (1H, m), 7.40 (1H, d), 7.30 (1H, m), 5.60 (2H, s), 3.15 (3H, s)

Example 43
3-(3-Bromo-4-methylphenyl)-4-(4-(methylsulfonyl)phenyl)-2-(5H)-furanone Analysis calculated for $C_{18}H_{15}BrO_4S$ C, 53.08; H, 3.71 Found: C, 53.06; H, 3.83

Example 44
3-(4-Bromo-2-fluorophenyl)-4-(4-(methylsulfonyl)phenyl)-2-(5H)-furanone Analysis calculated for $C_{17}H_{12}BrFO_4S$ C, 49.65; H, 2.94 Found: C, 49.76; H, 3.00

Example 45
3-(3,4-Dibromophenyl)-4-(4-(methylsulfonyl)phenyl)-2-(5H)-furanone $^1$H NMR (300 MHz, acetone-$d_6$) d 8.0 (2H, d), 7.80 (1H, d), 7.75 (3H, m), 7.25 (1H, d), 5.35 (2H, s), 3.15 (sH, s)

Example 46
3-(4-Chloro-3-fluorophenyl)-4-(4-(methylsulfonyl)phenyl)-2-(5H)-furanone Analysis calculated for $C_{17}H_{12}ClFO_4S$ C, 55.67; H, 3.30 Found: C, 55.45; H, 3.30

Example 47
3-(4-Bromo-3-fluorophenyl)-4-(4-(methylsulfonyl)phenyl)-2-(5H)-furanone Analysis calculated for $C_{17}H_{12}BrFO_4S$ C, 49.66; H, 2.94; S, 7.80 Found: C, 49.79; H, 3.01; S, 7.51

Example 48
3-(4-Bromo-2-chlorophenyl)-4-(4-(methylsulfonyl)phenyl)-2-(5H)-furanone Analysis calculated for $C_{17}H_{12}BrClO_4S$ C, 47.74; H, 2.83; S, 7.50 Found: C, 47.92; H, 2.84; S, 7.42

Example 49
3-(2-Naphthyl)-4-(4-(methylsulfonyl)phenyl)-2-(5H)-furanone

Analysis calculated for $C_{21}H_{16}O_4S$ C, 69.22; H, 4.43 Found: C, 69.22; H, 4.46

Example 50
3-(7-Quinolinyl)-4-(4-(methylsulfonyl)phenyl)-2-(5-H)-furanone

Analysis calculated for $C_{20}H_{15}NO_4S$ C, 65.74; H, 4.14; N, 3.83 Found: C, 65.34; H, 4.40; N, 3.80 M.S. (DCI, CH4) calculated for M+, 365 Found for M$^+$+1, 366

Example 51
3-(3.4-Dichlorophenyl)-4-(4-(aminosulfonyl)phenyl)-2-(2H)-furanone $^1$H NMR (400 MHz, $CD_3COCD_3$) d 7.92 (2H, dd), 7,64 (3H, dm), 7.60 (1H, dd), 7.32 (1H, dd), 6.70 (1H, bs), 5.38 (2H, s)

Example 52
3-(3.4-Difluorphenyl)-4-(4-(aminosulfonyl)phenyl)-2-(2H)-furanone $_1$H NMR (400MHZ, $CD_3COCD_3$) d 7.92 (2H,dd), 7,64 (2H,dd), 7.30–7.45 (2H,m), 7.22 (1H,m), 6.68 (2H, bs), 5.37 (2H,s)

Example 53
3-(3-Chloro-4-methoxyphenyl)-4(4-aminosulfonyl)phenyl)-2-(2H)-furanone Analysis calculated for $C_{17}H_{14}ClNO_5S$ C, 53.76; H, 3.72, N, 3.69 Found: C, 53.32; H, 3.84, N, 3.59 M.S. (Dcl, $CH_4$) calculated for M$^+$, 379 Found for M$^+$+1, 380

Example 54
3-(3-Bromo-4-methoxyphenyl)-4-(4-aminosulfonyl)phenyl)-2-(2H)-furanone Analysis calculated fro $C_{17}H_{14}BrNO_5S$ C, 48.13; H, 3.33, N, 3.30 Found: C, 48.26; H, 3.40, N) 3.28 M.S. (DCI, $CH_4$) calculated for M+, 423 Found for M$^+$+1, 424

In one aspect within this embodiment are the compounds of formula I

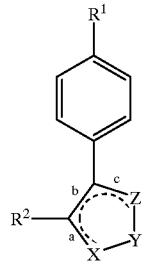

I or pharmaceutically acceptable salts thereof wherein:
X—Y—Z— is selected from the group consisting of —C(O)—O—CR$^5$(R$^{5'}$)—when side b is a double bond, and sides a and c are single bonds; and R$^1$ is selected from the group consisting of
  (a) S(O)$_2$CH$_3$,
  (b) S(O)$_2$NH$_2$, R$^2$ is selected from the group consisting of
  (a) C$_{1-6}$alkyl,
  (b) C$_3$, C$_4$, C$_5$, C$_6$, and C$_7$, cycloalkyl,
  (c) heteroaryl
  (d) benzoheteroaryl
  (e) mono- or di-substituted phenyl wherein the substituent is selected from the group consisting of
    (1) hydrogen,
    (2) halo,
    (3) C$_{1-6}$alkoxy,
    (4) C$_{1-6}$alkylthio, (5) CN,
(6) CF$_3$,
(7) C$_{1-6}$alkyl,
(8) N$_3$,
(9) —CO$_2$H,
(10) —CO$_2$—C$_{1-4}$alkyl,
(11) —C(R$^5$)(R$^6$)—OH,
(12) —C(R$^5$)(R$^6$)—O—C$_{1-4}$alkyl, and
(13) —C$_{1-6}$alkyl—CO$_2$—R$^5$;

R$^5$, R$^{5'}$ and R$^6$ are each independently selected from the group consisting of
(a) hydrogen,
(b) C$_{1-6}$alkyl, or R$^5$ and R$^6$ together with the carbon to which they are attached form a saturated monocyclic carbon ring of 3, 4, 5, 6 or 7 atoms.

An alternative genus encompases componds of formula Ib

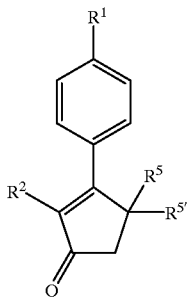

or a pharmaceutically acceptable salt thereof wherein:
R$^1$ is selected from the group consisting of
(a) S(O)$_2$CH$_3$,
(b) S(O)$_2$NH$_2$,
(c) S(O)$_2$NHC(O)CF$_3$,
(d) S(O)(NH)CH$_3$,
(e) S(O)(NH)NH$_2$,
(f) S (O)(NH)NHC(O)CF$_3$,
(g) P(O)(CH$_3$)OH, and
(h) P(O)(CH$_3$)NH$_2$, R$^2$ is selected from the group consisting of
(a) C$_3$, C$_4$, C$_5$, C$_6$, and C$_7$, cycloalkyl,
(b) mono-, di- or tri-substituted phenyl wherein the substituent is selected from the group consisting of
(1) hydrogen,
(2) halo,
(3) C$_{1-6}$alkoxy,
(4) C$_{1-6}$alkylthio,
(5) CN,
(6) CF$_3$,
(7) C$_{1-6}$alkyl,
(8) N$_3$,
(9) —CO$_2$H,
(10) —CO$_2$—C$_{1-4}$alkyl,
(c) mono-, di- or tri-substituted heteroaryl wherein the heteroaryl is a monocyclic aromatic ring of 5 atoms, said ring having one hetero atom which is S, O, or N, and optionally 1, 2, or 3 additional N atoms; or the heteroaryl is a monocyclic ring of 6 atoms, said ring having one hetero atom which is N, and optionally 1, 2 or 3 additional N atoms; said substituents are selected from the group consisting of
(1) hydrogen,
(2) halo, including fluoro, chloro, bromo and iodo,
(3) C$_{1-6}$alkyl,
(4) C$_{1-6}$alkoxy,
(5) C$_{1-6}$alkylthio,
(6) CN,
(7) CF$_3$,
(8) N$_3$, R$^5$ and R$^{5'}$ are each independently selected from the group consisting of
(a) hydrogen,
(b) C$_{1-6}$alkyl, with the proviso that at least one of R$^5$ and R$^{5'}$ is C$_{1-6}$alkyl.

Within this genus is the sub-genus of compounds wherein
R$^2$ is selected from the group consisting of
(a) cyclohexyl, and
(b) mono- or di-substituted phenyl, and wherein the substitutents are selected from the group consisting of
(1) hydrogen,
(2) halo,
(3) C$_{1-4}$alkoxy,
(4) C$_{1-4}$alkylthio,
(5) CN,
(6) CF$_3$,
(7) C$_{1-4}$alkyl,
(8) N$_3$, and R$^5$ and R$^{5'}$, R$^6$, are each independently selected from the group consisting of
(a) hydrogen,
(b) methyl or ethyl, with the proviso that at least one of R$^5$ and R$^{5'}$ is C$_{1-6}$alkyl.

Within his sub-genus there is a class of compounds wherein
R$^1$ is selected from the group consisting of
(a) S(O)$_2$CH$_3$,
(b) S(O)$_2$NH$_2$,
(c) S(O)NHCH$_3$, and
(d) S(O)NHNH$_2$;

R$^2$ is
mono or di-substituted phenyl wherein the substitutents are selected from the group consisting of
(1) hydrogen,
(2) halo, selected from the group consisting of fluoro, chloro and bromo,
(3) methoxy, and
(4) methyl.

Within this class is a sub-class of compounds wherein R$^1$ is selected from the group consisting of
(a) S(O)$_2$CH$_3$, and
(b) S(O)$_2$NH$_2$, R$^2$ is
mono or di-substituted phenyl wherein the substitutents are selected from the group consisting of
(1) hydrogen,
(2) halo, selected from the group consisting of fluoro, chloro and bromo;

R$^5$ and R$^{5'}$ are each independently methyl.

Illusttrating this sub-class are the compounds wherein R$^1$ is selected from the group consisting of
(a) S(O)$_2$CH$_3$, R$^2$ is
mono or di-substituted phenyl wherein the substitutents are halo, selected from the group consisting of fluoro, chloro and bromo.

Exemplifying this sub-class are the compounds selected from (1) 5,5-Dimethyl-3-(4-fluorophenyl)-4-(4-methylsulfonyl)phenyl)-2-(5H)-furanone, (2) 5,5-Dimethyl-3-(3-fluorophenyl)-4-(4-methylsulfonyl)phenyl)-2-(5H)-furanone, (3) 5,5-Dimethyl-3-(3-chlorophenyl)-4-(4-methylsulfonyl)phenyl)-2-(5H)-furanone, (4) 5,5-Dimethyl-3-(3,4-difluorophenyl)-4-(4-methylsulfonyl)phenyl)-2-(5H)-furanone, (5) 5,5-Dimethyl-3-(3,4-dichlorophenyl)-4-(4-methylsulfonyl)phenyl)-2-(5H)-furanone, (6) 5,5-Dimethyl-3-(4-chlorophenyl)-4-(4-methylsulfonyl)phenyl)-2-(5H)-furanone, (7) 5,5-Dimethyl-3-(2-naphyhyl)-4-(4-(methylsulfonyl)phenyl)-2-(5H)-furanone, or a pharmaceutically acceptable salt thereof, as well as

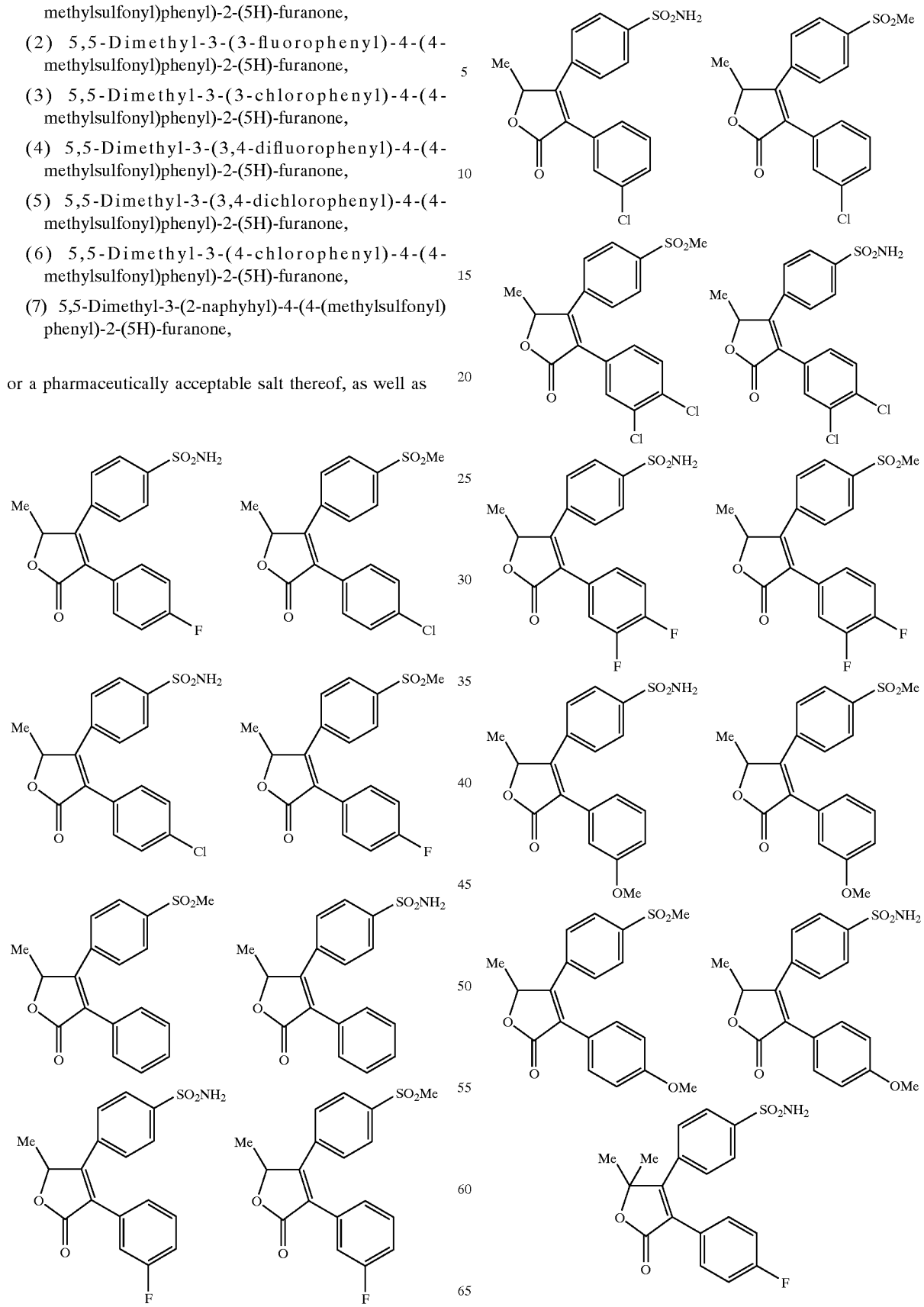

or a pharmaceutically acceptable salt thereof.

In an alternative aspect the invention is directed to a method of treating a disease in humans selected from stroke, cerebral ischemia and de-myelinating disorders which comprises administering to said human an effective amount of a non-steroidal COX-2 inhibitor, wherein said non-steroidal COX-2 inhibitor will bind at least 100 times as well to COX-2 as to COX-1.

An alternative preparation of the hydroxy ketone XLIII is the oxidation of the known (J. Org. Chem. 1991 56, 5955-8; Sulfur Lett. 1991, 12, 123-32) ketone XLVII. A mixture of XLVII, aqueous base, such as NaOH, organic solvents such as carbon tetrachloride/toluene and a phase transfer catalyst such as ALIQUAT 336 is stirred in air at room temperature to provide XLIII. Compound XLIII is also described in U.S. 4,321,118 and Org. Coat. 1986, 6, 175-95.

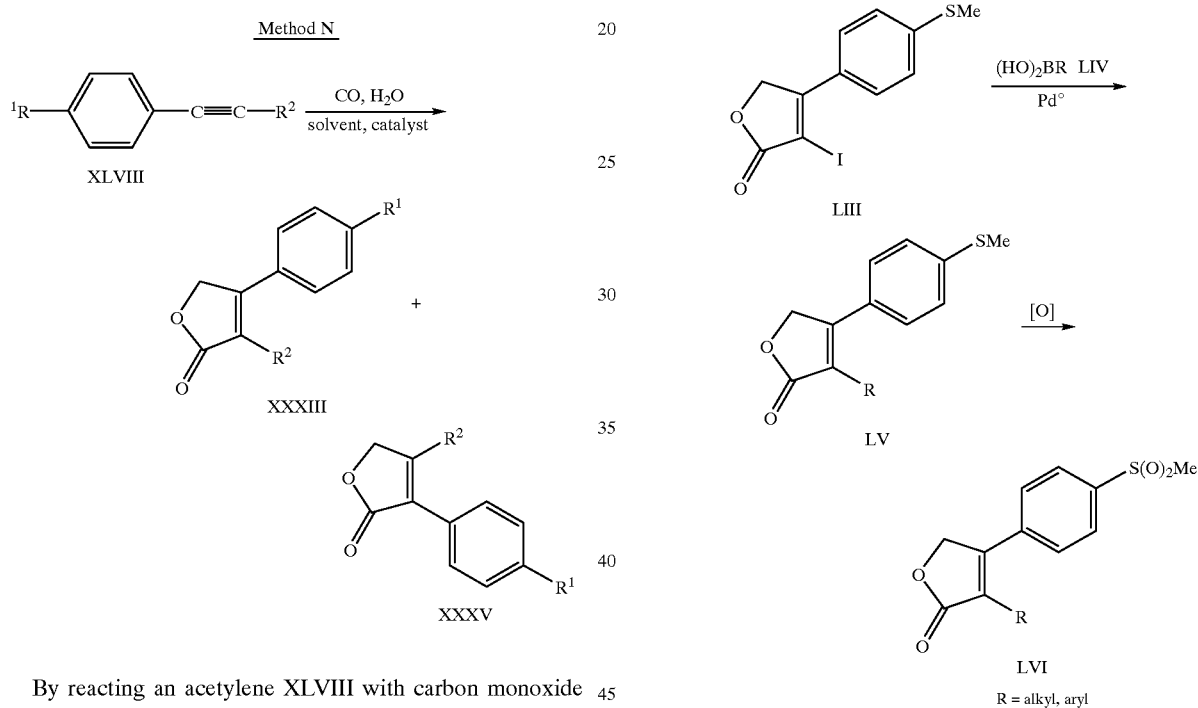

By reacting an acetylene XLVIII with carbon monoxide and water in the presence of suitable catalysts, a mixture of compound XXXIII and its isomer XXXV is obtained. The isomers are separable by standard procedures in the art such as chromatography or crystallization. Examples of useful catalysts and conditions are $PdCl_2$ in aqueous HCl and EtOH, heated at 50–150$_t$C and 50–150 atmospheres of pressure, or $Rh_4(CO)_{12}$ (or $Rh_6(CO)_{16}$) in aqueous THF (or acetone, acetonitrile, benzene, toluene, EtOH, MeOH) containing a trialkylamine, at 50–150$_t$C and 20–300 atmospheres pressure. See Takahashi et al., *Organomettallics* 1991, 10, 2493–2498; and Tsuji et. al., *J. Am. Chem. Soc.* 1966, 88, 1289–1292.

1,4-Addition to XLIX of 4-methylthiophenyl organometallic reagents L in the presence of copper salts and the trapping of the resultant enolate with trialkyl silyl chloride such as TMSCl or TIPSCl provide the ketene acetal LI. The ketene acetal can then be oxidized to the substituted butenolide LII by the method of Ito using catalytic amounts of $Pd_2(OAC)_2$ and $Cu(OAc)_2$ and $O_2$ in MeOH or by the method of Magnus using $PhIO/TMSN_3$ and $Bu_4NF$. Introduction of the iodine can be accomplished by treating LII with $I_2$ in the presence of pyridine to afford LIII. Palladium catalyzed Susuki or Stille coupling of LIII with the appropriate aryl or alkyl partner such as the boronic acid LIV provides the butenolide LV. The sulfide can be oxidized to a sulfone by various oxidizing agents such as peracetic acid, MPPM, MMPP or $H_2O_2$ to give the desired compound LVI. See Y. Ito et. al., *J. Am. Chem. Soc.* 1979, 101, 494; and P. Magnus et. al., *Tet. Lett.* 1992, 2933.

METHOD P

Where R² is phenyl or mono- or disubstituted phenyl or heteroaryl or mono- or disubstituted heteroaryl.

Hydroxy ketone XLIII can be oxidized to the sulfone LVII by a suitable oxidizing agent such as OXONE$^R$. By reacting the hydroxy sulfone LVII with an appropriately substituted aryl acetic acid in an inert solvent in the presence of a dehydrating agent such as a carbodiimide and a catalytic amount of DMAP, ester LVIII can be obtained. Treatment of ester LVIII with a base such as DBU in an inert solvent affords the lactone LIX.

See also WO 95/00501, published Jan. 5, 1995, which is hereby incorporated by reference.

Example 55
5-(4-(Methylsulfonyl)phenyl)-4-(4-fluorophenyl)-isothiazole
M.S. (DCI, CH$_4$) calculated for M$^+$, 333 Found for M$^+$+1, 334

Example 56
3-(3-Chlorophenyl)-5,5,-dimethyl-4-(4-(methylsulfonyl)phenyl)-2-(5H)-furanone
$^1$H NMR (400 MHz, CDCl$_3$) d 8.00 (2H, d), 77.13–7.42 (6H, m), 3.08 (3H, s), 1.59 (6H, s).
Cox-1 (microsome) IC$_{50}$>100μM Cox-2 (whole cell) IC$_{50}$=31 nM

Example 57
5,5-Dimethyl-3-(2-naphthyl)-4-(4-(methylsulfonyl)phenyl)-2-(5H)-furanone
Analysis calculated for C$_{23}$H$_{20}$O$_4$S C, 70.39; H, 5.19
Found: C, 69.99; H, 5.19 M.S. (DCI, CH$_4$) calculated for M$^+$, 392 Found for M$^+$+1, 393
Cox-1 (microsome) IC$_{50}$=approx. 50 μM Cox-2 (whole cell) IC$_{50}$=97 nM

Example 58
3-(3,4-Difluorophenyl)-5,5,-dimethyl-4-(4-(methylsulfonyl)phenyl)-2-(5H)-furanone
Analysis calculated for C$_{19}$H$_{16}$F$_2$O$_4$S C, 60.31; H, 4.26; S, 8.47 Found: C, 60.46; H, 4.34; S, 8.55 m.p. 191 ₜC
Cox-1 (microsome) IC$_{50}$>100 μM Cox-2 (whole cell) IC$_{50}$=13 nM

Example 59
3-(3.4-Dichlorophenyl)-5,5-dimethyl-4-(4-(methylsulfonyl)phenyl)-2-(5H)-furanone
Analysis calculated for C$_{19}$H$_{16}$Cl$_2$O$_4$S C, 55.48; H, 3.92; S, 7.80 Found: C, 55.65; H, 3.96; S, 8.04 m.p. 184–185 ₜC
Cox-1 (microsome) IC$_{50}$ >100 μM Cox-2 (whole cell) IC$_{50}$=13 nM

Example 60
3-(4-Chlorophenyl)-5,5,-dimethyl-4-(4-(methylsulfonyl)phenyl)-2-(5H)-furanone
Analysis calculated for C$_{19}$H$_{17}$ClO$_4$S C, 60.56; H, 4.55 Found: C, 60.44; H, 4.11 M.S. (DCI, CH$_4$) calculated for M$^+$, 376 Found for M$^+$+1, 377
Cox-1 (microsome) IC$_{50}$>100 μM Cox-2 (whole cell) IC$_{50}$=46 nM

Example 23

(alternative 1)
3-(Phenyl)-4-(4-(methylsulfonyl)phenyl)-2-(5H)-furanone
Into a 20 ml glass ampule are added 1 g of 2-(4-(methylsulfonyl)phenyl)phenylacetylene, 20 mg of Rh$_4$(CO)$_{12}$, 1.5 g of Et$_3$N, 10 ml of THF, 1 ml of water under nitrogen atmosphere, and the ampule is placed in a 100-ml stainless steel autoclave. The reaction system is flushed three times with CO then charged at room temperature to a initial CO pressure of 100 atm. The reaction is carried at 100 ₜC for 5 h. The solution is then diluted with 50 ml of benzene and washed with brine, iN HCl. The benzene solution is dried over Na$_2$SO$_4$, and concentrated. The crude products are separated by column chromatography on silica gel eluted with 2:1 EtOAc/hexane to give the title compound and its regioisomer.

Example 23

(alternative 2)
3-(Phenyl)-4-(4-(methylsulfonyl)phenyl)-2-(5H)-furanone
Step 1: 2-trimethylsilyloxy-4-(4-(methylthio)phenyl)-3.4-dihydrofuran
To a solution of 3.86 g (19 mmol) of 4-bromothioanisole in 90 mL of Et$_2$O cooled at −78ₜC, is added 22 mL of 1.7 M solution of t-BuLi in pentane (38 mmol) dropwise. The reaction mixture is stirred for 15 min at −78 °C and 3.8 g of CuI is added and the reaction mixture is allowed to warm to −40 °C over a period of 30 min. A solution of 1.7 g of 2(5H)-furanone in 10 ml of THF is added. After stirring for 1 h, 2 ml of freshly distilled TMSCl is added dropwise. The reaction mixture is then treated with 2 ml of $Et_3N$ and 50 ml of sat. $NaHCO_3$, and extracted with 100 ml of ether. The ether layer is dried over $Na_2SO_4$ and concentrated to the crude title compound which is used for the next step without further purification.

Step 2: 4-(4-(methylthio)phenyl)-2-(5H)-furanone

To a solution of 4 g of $Pd(OAc)_2$ in 100 ml of acetonitrile is added dropwise the crude product from Step 1(5 g) under nitrogen at room temperature. After 10 h at room temperature, the mixture is condensed under reduced pressure and the residue is purified by flash chromatography on silica gel eluted with 2:1 hexane/EtOAc to give the title compound.

Step 3: 3-iodo-4-(4-(methylthio)phenyl)-2-(5H)-furanone

To a solution of 3 g of the product of Step 2 in 30 ml of pyridine is added 8.7 g of $I_2$. The mixture is stirred for 24 h and then diluted with 200 ml of ether, washed with 100 ml of 5N HCl and 50 ml of 5N $Na_2S_2O_3$. The ether layer is dried over $Na_2SO_4$ and concentrated to give the title compound.

Step 4: 3-(Phenyl)-4-(4-(methylthio)phenyl)-2-(5H)-furanone

A mixture of 4 g of the product of Step 3, 3.7 g of $PhB(OH)_2$, 0.4 g of $Ph_3As$, 0.4 g of $PdCl_2(PhCN)_2$ in 100 ml of benzene and 15 ml of 2N NaOH is refluxed for 6 h. Ether(200 ml) is then added and the mixture is washed with 100 ml of saturated $NaHCO_3$. The organic layer is dried over $MgSO_4$ and concentrated. The residue is purified by flash chromatography on silica gel eluted with 4:1 hexane/EtOAc to give the tide compound.

Step 5: 3-(Phenyl)-4-(4-(methylsulfonyl)phenyl)-2-(5H)-furanone

To a solution of 3 g of the product of Step 4 in 80 mL of 10:1 $CH_2Cl_2$/MeOH is added 5.5 g of MPPM. The reaction mixture is stirred at room temperature for 2 h and then diluted with 100 mL of 1: 1 hexane/EtOAc. After filtration and concentration, the residue is purified by flash chromatography eluted with 2:1 EtOAc/hexane to give the title product.

Example 61
5,5-Dimethyl-3-(3-fluorophenyl)-4-(4-(methylsulfonyl) phenyl)-2-(5H)-furanone Step 12-hydroxy-4-(methylsulfonyl)isobutyrophenone To a solution of 2-hydroxy-4'-(methylthiol) isobutyrophenone (45 g) in t-BuOH (500 mL) and $CH_2Cl_2$ (200 mL) was added a solution of OXONE™ (194 g) in $H_2O$ (1.4 L). The reaction mixture was stirred for 18 h at r.t. and then extracted with EtOAc (3 x 500 mL). The organic extracts were combined and dried over $Na_2SO_4$ and the solvent was evaporated. The residue was swished in ether/hexane to give the title compound as a yellow solid (47.4 g).

Step 23-Fluorophenylacetic acid, 1,1-dimethyl-2-(4-(methylsulfonyl)phenyl)-2-oxo-ethyl ester A mixture of 2-hydroxy-4'-(methylsulfonyl) isobutyrophenone (100 g), 3-fluorophenylacetic acid (83 g), 1-cyclohexyl-3-(2-morpholinoethyl)carbodiimide metho-p-toluenesulfonate (225 g) and DMAP (25 g) in $CH_2Cl_2$ (2 L) was mechanically stirred for 17 h at r.t.. A solution of IN HCl (1 L) was then added and the organic phase was separated, washed with a saturated solution of $Na_2CO_3$ (0.4 L) and dried over $MgSO_4$. After concentration, the residue was purified by silica gel chromatography, eluting with 30% EtOAc/hexane to give the tide compound as a white solid (133 g).

Step 35,5-Dimethyl-3-(3-fluorophenyl)-4-(4-(methylsulfonyl)phenyl))-2-(5H)-furanone A solution of the product from Step 2 (120 g) in $CH_2Cl_2$ (1 L) was treated with DBU (81.6 g) and stirred for 1 h at r.t.. The reaction mixture was then treated with IN HCl (550 mL) and the organic phase was separated, washed with saturated $NaHCO_3$ and dried over $MgSO_4$. After concentration, the crude was swished from 20% EtOAc/hexane (450 niL) to give the tide compound as a white solid (108.4 g, m.p. 172.7°C).

Analysis Calculated C 63.32; H 4.75 Found: C 63.50; H 4.79

Cox-1 (microsome) $IC_{50}$>100 µM Cox-2 (whole cell)$IC_{50}$ 37 nM

Rat pyresis $ED_{50}$=1.47

What is claimed is:

1. A method of treating pre-senile dementia associated with Alzheimer's disease in a human in need of such treatment which comprises administering to said human an effective amount of a non-steroidal COX-2 inhibitor, wherein said non-steroidal COX-2 inhibitor will bind at least 100 times as well to COX-2 as to COX-1.

2. A method according to claim 1 wherein the administration is oral administration.

3. A method according to claim 2 wherein the non-steroidal COX-2 inhibitor is within a tablet or capsule.

4. A method of treating senile dementia in a human in need of such treatment which comprises administering to said human an effective amount of a non-steroidal COX-2 inhibitor, wherein said non-steroidal COX-2 inhibitor will bind at least 100 times as well to COX-2 as to COX-1.

5. A method according to claim 4 wherein the administration is oral administration.

6. A method according to claim 5 wherein the non-steroidal COX-2 inhibitor is within a tablet or capsule.

* * * * *